US006369223B2

(12) United States Patent
Jacobsen et al.

(10) Patent No.: US 6,369,223 B2
(45) Date of Patent: *Apr. 9, 2002

(54) ASYMMETRIC CYCLOADDITION REACTIONS

(75) Inventors: Eric N. Jacobsen, Boston; Scott E. Schaus, Cambridge; Alexander G. Dossetter, Somerville; Timothy F. Jamison, Cambridge, all of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/755,612

(22) Filed: Jan. 4, 2001

Related U.S. Application Data

(63) Continuation of application No. 09/255,480, filed on Feb. 23, 1999, now Pat. No. 6,211,370, which is a continuation-in-part of application No. 09/006,104, filed on Jan. 13, 1998, now Pat. No. 6,130,340.

(51) Int. Cl.$^7$ ...................... C07D 285/15; C07D 513/04
(52) U.S. Cl. ............................. 544/4; 544/47; 502/182; 502/210; 502/219; 502/305
(58) Field of Search ........................ 544/4, 47; 502/182, 502/210, 219, 305

(56) References Cited

U.S. PATENT DOCUMENTS

| 5,352,814 A | 10/1994 | Katsuki et al. |
| 5,491,266 A | 2/1996 | Babin et al. |
| 5,665,890 A | 9/1997 | Jacobsen et al. ............ 549/230 |

FOREIGN PATENT DOCUMENTS

| GB | 2 304 339 A | 3/1997 |
| JP | 9-67274 | 3/1997 |
| WO | WO 93/03838 | 3/1993 |
| WO | WO 96/21507 | 7/1996 |
| WO | WO 99/36375 | 7/1999 |

OTHER PUBLICATIONS

Bednarski, M., et al., "On the Interactivity of Chiral Auxiliaries with Chiral Catalysts in the Hetero Diels–Alder Reaction: A New Route to L–Glycolipids", *American Chemical Society*, 0002–7863/83/1505–6968, (1983).

Bednarski, M., et al., "Mild Lewis Acid Catalysis: Eu(fod)3–Mediated Hetero–Diels–Alder Reaction", *American Chemical Society*, 0002–7863/83/1505–3716, 1983.

Collman, J. P., et al., "Regioselective and Enantioselective Epoxidation Catalyzed by Metalloporphyrins", *Science*, vol. 261, (Sep. 10, 1993).

Corey, E.J., et al., "First Application of Attractive Intramolecular Interactions to the Design of Chiral Catalysts for Highly Enantioselective Diels–Alder Reactions", *J. Am. Chem. Soc.*, 113, 8966–8967, (1991).

Corey, E.J., et al., "Enantioselective Mukaiyama–Aldol and Aldol–Dihydropyrone Annulation Reactions Catalyzed By A Tryptophan–Derived Oxazaborolidine", *Tetrahedron Letters*, vol. 33, No. 46, pp. 6907–6910, (1992).

Danishefsky S.J., et al., "Totally Synthetic Routes to the Higher Monosaccharides", *Angew. Chem. Int. Ed. Engl.* 26, pp. 15–23, (1987).

Gao, Qingzhi, et al., "Asymmetric Hetero Diels–Alder Reaction Catalyzed by Stable and Easily Prepared CAB Catalysts", *J. Org. Chem.*, 57, pp. 1951–1952, (1992).

Ghosh, A.K., et al., "Synthetic Studies Of Antitumor Macrolide Laulimalide: Enantioselective Synthesis Of The C3–C–14 Segment By A Catalytic Hetero Diels–Alder Strategy", *Tetrahedron Letters*, vol. 38, No. 14, pp. 2427–2430 (1997).

Hu, Y.J., et al., "Formal Synthesis of 3–Deoxy–D–manno–2–Octulosonic Acid (KDO) via a Highly Double–Stereoselective Hetero Diels–Alder Reaction Directed by a (Salen) Coll Catalyst and Chiral Diene", *J. Org. Chem.*, vol. 63, pp. 2456–2461, (1998).

Jacobsen, E.N., et al., "Electronic Tuning of Asymmetric Catalysts", *J. Am. Chem. Soc.*, vol. 113, pp. 6703–6704, (1991).

Keck, G.E., et al., "Catalytic Enantioselective Synthesis of Dihydropyrones via Formal Hetero Diels–Alder Reactions of "Danishefsky's Diene" with Aldehydes", *J. Org. Chem.*, vol. 60, pp. 5998–5999, (1995).

Larrow, J.F., et al., "A Practical Method for the Large–Scale Preparation of [N,N–Bis (3,5–tert–butylsalicylidene)–1, 2–cyclohexanediaminato (2–)]manganese (III) Chloride, a Highly Enantioselective Epoxidation Catalyst", *J. Org. Chem.*, vol. 59, pp. 1939–1942 (1994).

Larrow, J.R., et al., "Kinetic Resolution of 1,2–Dihydronaphthalene Oxide and Related Epoxides via Asymmetric C–H Hydroxylation", *J. Am. Chem. Soc.*, vol. 116, pp. 12129–12130, (1994).

Lee, N.H., et al., "Enantiomerically Pure Epoxychromans via Asymmetric Catalysis", *Tetrahedron Letters*, vol. 32, No. 38, pp. 5055–5058, (1991).

(List continued on next page.)

Primary Examiner—T. A. Solola
(74) Attorney, Agent, or Firm—Dana M. Gordon; Foley, Hoag & Eliot LLP

(57) ABSTRACT

The present invention relates to a process for stereoselective cycloaddition reactions which generally comprises a cycloaddition reaction between a pair of substrates, each either chiral or prochiral, that contain reactive π-systems, in the presence of a non-racemic chiral catalyst, to produce a stereoisomerically enriched product. The present invention also relates to novel asymmetric catalyst complexes comprising a metal and an asymmetric tridentate ligand.

28 Claims, No Drawings

OTHER PUBLICATIONS

Matsukawa, S., et al., "Importance of chiral activators in the asymmetric catalysis of Diels–Alder reactions by chiral titanium (IV) complexes", *Tetrhedron: Asymmetry,* vol. 8, No. 6, pp. 815–816 (1997).

Palucki, M., et al., "Asymmetric Oxidation of Sulfides with H2O2 Catalyzed by (salen) MN (III) Complexes", *Tetrahedron Letters,* vol. 33, No. 47, pp. 7111–7114 (1992).

Sasaki, H., et al., "Rational Design of Mn–Salen Catalyst (2): Highly Enantioselective Epoxidation of Conjugated cis–Olefins", *Tetrahedron,* vol. 50, No. 41, pp. 11827–11838 (1994).

Zhang, W., et al., "Enantioselective Epoxidation of Unfunctionalized Olefins Catalyzed by (Salen) manganese Complexes", *J. Am. Chem. Soc.,* vol. 112, pp. 2801–2803 (1990).

Zhang, W., et al., "Asymmetric Olefin Epoxidation with Sodium Hypochlorite Catalyzed by Easily Prepared Chiral Mn (III) Salen Complexes", *J. Org. Chem.,* vol. 56, pp. 2296–2298 (1991).

Yao, S., et al., "Catalytic Asymmetric Hetero–Diels–Alder Reactions of Ketones: Chemzymatic Reactions," *American Chemical Society,* 120, pp. 8599–8605, 1998.

Evans, et al., "Catalytic Enantioselective Hetero Diels–Alder Reactions of a, B–Unsaturated Acyl Phosphonates with Enol Ethers", *J. Am. Chem. Soc.,* vol. 120, pp. 4895–4896, 1998.

Otto, S., et al., "A Chiral Lewis–Acid–Catalyzed Diels–Alder Reaction. Water–Enhanced Enantioselectivity", *J. Am. Chem. Soc.,* 120, pp. 4238–4239 (1998).

Gao, Qingzhi et al., "Asymmetric Hetero Diels–Alder Reaction Catalyzed by Stable and Easily Prepared CAB Catalysts", *Tetrahedron* 4:979–988 (1994).

Johannsen, Mogens, et al., "The first highly enentioselective catalytic hetero–Diels–Alder reaction of ketone", *Chem. Comm.,* 2169–2170 (1997).

Li, L.–S. et al., "Asymmetric hetero–Diels–Alder reaction of 1–alkyl–3silyoxy–1,3–diens with ethyl glyoxate catalyzed by a chiral (salen)cobalt(II) complex", *Tetrahedron: Asymmetry,* 9:2271–2277 (1998).

Schaus, S. et al., "Asymmetric Hetero–Diels–Alder Reactions Catalyzed by Chiral (Salen)Chromium(III) Complexes", *J. Org. Chem.,* 63:403–405 (1998).

Yao, Sulan et al., "Zinc(II)–catalysed asymmetric hetero–Diels–Alder reactions of conjugated dienes with glyoxylate", *J. Chem. Soc., Perkins Trans.,* 1:2345–2349 (1997).

ASYMMETRIC CYCLOADDITION REACTIONS

RELATED APPLICATIONS

This application is a continuation of U.S. Ser. No. 09/255,480, filed Feb. 23, 1999 now U.S. Pat. No. 6,211,370; which is a continuation-in-part of U.S. Ser. No. 09/006,104, filed Jan. 13, 1998, now U.S. Pat. No. 6,130,340, issued Oct. 10, 2000.

GOVERNMENT FUNDING

The present invention was made with support from the National Institutes of Health; the government, therefore, has certain rights in the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. The advantages of enantiomerically pure compounds (reviewed in, e.g., Stinson, S. C., *Chem Eng News*, Sept. 28, 1992, pp. 46–79) include fewer side effects and greater potency in many cases.

Traditional methods of organic synthesis have often been optimized for the production of racemic materials. The production of enantiomerically pure material has historically been achieved in one of two ways: the use of enantiomerically pure starting materials derived from natural sources (the so-called "chiral pool"); or the resolution of racemic mixtures by classical techniques. Each of these methods has serious drawbacks, however. The chiral pool is limited to compounds found in nature, so only certain structures and absolute configurations are readily available. Resolution of racemates often requires the use of resolving agents; this process may be inconvenient and is certain to be time-consuming. Furthermore, resolution often means that the undesired enantiomer is discarded, thereby wasting half of the material.

Cycloaddition reactions are powerful, frequently-exploited elements of the palette of transformations available to the synthetic organic chemist. There are numerous reasons for the importance of cycloaddition reactions, inter a/ia: 1) they are concerted reactions; 2) their products are significantly more complex than the required starting materials; 3) the relative simplicity and synthetic accessibility of the required starting materials; and 4) they are capable of generating a number of stereocenters in a single operation. The first of these points is tremendously important because concerted reactions transmit to their products in well-understood ways the stereochemical information contained in their starting materials.

The synthetic utility of cycloaddition reactions in which one of the reactants is a carbonyl group or analogue thereof—termed "Hetero"-cycloadditions—has been further expanded by progress in the development of asymmetric catalysts for these reactions. The Hetero-Diels-Alder reaction is perhaps the best example of a cycloaddition reaction whose utility has been has been augmented by research directed at the development of asymmetric catalysts (for a review, see: Danishefsky Chemtracts. *Organic Chemistry* 1989, 273). Catalysts comprising a transition metal ion and a chiral, non-racemic ligand have been reported to render enantioselective various Hetero-Diels-Alder cycloadditions; these reactions gave products in good to excellent enantiomeric excess (for leading references, see: Danishefsky and DeNinno, *Angew. Chim., Intl. Ed. Engl.* 1987, 26, 15–23; Corey and Loh, *J. Am. Chem. Soc.*, 1991, 113, 8966–8967; Yamamoto et al.,*J. Org. Chem.*, 1992, 57, 1951–1952; Keck et al.,*J. Org. Chem.*, 1995, 60, 5998–5999; and Ghosh et al., *Tetrahedron Lett.* 1997, 38, 2427–2430).

The cyclohexene ring generated in a Diels-Alder reaction can be incorporated without further modification into biologically-active natural products, drug candidates, and pharmaceuticals. Additionally, the newly-formed cyclohexene ring may serve as a starting point for further synthetic transformations. For example, the A, B, and C rings of the steroid skeleton are functionalized cyclohexane rings; a number of routes to steriods based on the Diels-Alder reaction have been reported. The olefin in the cyclohexene derived from a Diels-Alder reaction can serve as a functional handle for subsequent transformations. The Diels-Alder reaction tolerates a wide range of "spectator" functionality—functionality not involved in, or affected by, the reaction conditions—which can serve as reactive sites in subsequent transformations. Finally, the so-called Hetero-Diels-Alder reaction provides access to unsaturated six-membered heterocycles.

SUMMARY OF THE INVENTION

In one aspect of the present invention, there is provided a process for enantioselective chemical synthesis which generally comprises reacting a diene and an aldehyde in the presence of a non-racemic chiral catalyst to produce a enantiomerically enriched dihydropyran product. The diene substrate comprises a 1,3-diene moiety, the dienophile comprises a single reactive π-bond, and the chiral catalyst comprises an asymmetric tetradentate or tridentate ligand complexed with a transition metal ion. In the instance of the tetradentate ligand, the catalyst complex has a rectangular planar or rectangular pyrimidal geometry. The tridentate ligand-metal complex has a trigonal pyrimidal or planar geometry. In a preferred embodiment, the ligand has at least one Schiff base nitrogen complexed with the metal core of the catalyst. In another preferred embodiment, the ligand provides at least one stereogenic center within two bonds of a ligand atom which coordinates the metal.

In general, the metal atom is a main group metal or transition metal from Groups 3–12 or from the lanthanide series, and is preferably not in its highest state of oxidation. For example, the metal can be a late transition metal, such as selected from the Group 5–12 transition metals. In certain embodiments, the metal atom is selected from the group consisting of Na, K, Rb, Mg, Ca, Sr, B, Al, Ga, In, Si, Ge, and Sn. In certain embodiments, the metal atom is selected from the group consisting of Co, Cr, Mn, V, Fe, Mo, W, Ru and Ni.

Exemplary diene substrates for the subject reaction include 1,3-dienes in which any or all of the heavy atoms comprising the backbone of said 1,3-diene are chosen from the set containing C, N, O, S, and P.

In preferred embodiments, the subject transformation can be represented as follows:

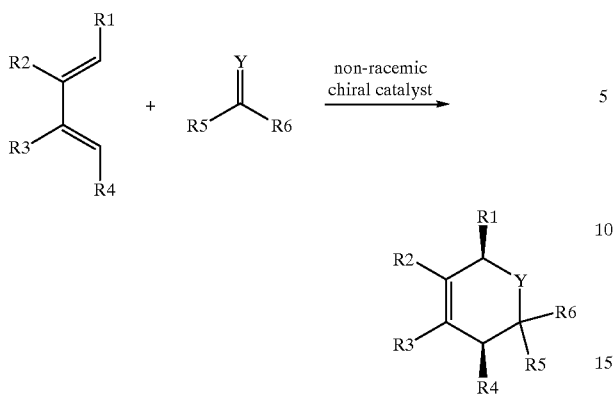

wherein

Y represents O, S, or NR$_7$;

R$_1$, R$_2$, R$_3$, R$_4$, R$_5$ and R6 each independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—R$_8$;

any two or more of the substituents R$_1$, R$_2$, R$_3$, R$_4$, R$_5$ and R$_6$ taken together may form a carbocylic or heterocyclic ring having from 4 to 8 atoms in the ring structure;

R$_8$ represents an aryl, a cycloalkyl, a cycloalkenyl, a heterocycle or a polycycle; and m is zero or an integer in the range of 1 to 8.

In certain embodiments, R$_1$, R$_2$, R$_3$, and R$_4$ are chosen such that the substrate has a plane of symmetry.

Exemplary dienophile substrates for the subject reaction include aldehydes, ketones, esters, amides, carbonates, thioaldehydes, thioamides, thiocarbonates, lactones, lactams, thiollactones, thiolactams, imines, oximes, hydrazones, thionoesters, thioesters, dithioesters, thionolactones, thiolactones, dithiolactones, phosphorus ylides, thioketones, acid halides, anhydrides, imines, iminium ions, imines, oximes, oximes, hydrazones, nitroso-containing compounds, nitro-containing compounds, compounds containing a phosphorus-oxygen π-bond, and compounds containing a phosphorus-sulfur π-bond.

In a preferred embodiment, the method includes combining a diene, a dienophile, and a non-racemic chiral catalyst as described herein, and maintaining the combination under conditions appropriate for the chiral catalyst to catalyze an enantioselective cycloaddition reaction between the two substrates.

In certain embodiments, the chiral catalyst which is employed in the subject reaction is represented by the general formula:

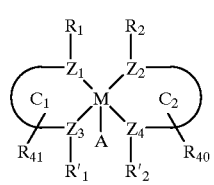

wherein

Z$_1$, Z$_2$, Z$_3$ and Z$_4$ each represent a Lewis base;

the C$_1$ moiety, taken together with Z$_1$, Z$_3$ and M, and the C$_2$ moiety, taken together with Z$_2$, Z$_4$ and M, each, independently, form a heterocycle;

R$_1$, R$_2$, R'$_1$ and R'$_2$ each, independently, are absent or represent a covalent substitution with an organic or inorganic substituent permitted by valence requirements of the electron donor atom to which it is attached;

R$_{40}$ and R$_{41}$ each independently are absent, or represent one or more covalent substitutions of C$_1$ and C$_2$ with an organic or inorganic substituent permitted by valence requirements of the ring atom to which it is attached;

any two or more of the R$_1$, R$_2$, R'$_1$, R'$_2$ R$_{40}$ and R$_{41}$ taken together may form a bridging substituent;

with the proviso that C$_1$ is substituted at least once by R$_1$, R'$_1$ or R$_{41}$, and C$_2$ is substituted at least once by R$_2$, R'$_2$ or R$_{40}$, and at least one of R$_1$, R'$_1$ and R$_{41}$ is taken together with at least one of R$_2$, R'$_2$ and R$_{40}$ to form a bridging substituent so as to provide Z$_1$, Z$_2$, Z$_3$ and Z$_4$ as a tetradentate ligand;

M represents the metal ion; and

A represents a counterion, wherein each R$_1$, R$_2$, R'$_1$, R'$_2$ R$_{40}$ and R$_{41}$ are selected to provide at least one stereogenic center in the tetradentate ligand.

In exemplary embodiments, R$_1$, R$_2$, R'$_1$ and R'$_2$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH2)$_m$—R$_8$;

each R$_{40}$ and R$_{41}$ occuring in 100 independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH2)$_m$—R$_8$;

R$_8$ represents an aryl, a cycloalkyl, a cycloalkenyl, a heterocycle or a polycycle;

Z$_1$, Z$_2$, Z$_3$ and Z$_4$ are independently selected from the group consisting of nitrogen, oxygen, phosphorus, arsenic, and sulfur; and m is zero or an integer in the range of 1 to 8.

For example, the catalyst can be represented by the general formula:

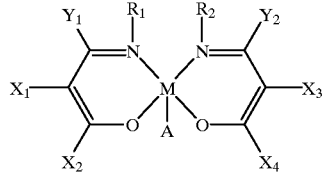

wherein the substituents R$_1$, R$_2$, Y$_1$, Y$_2$, X$_1$, X$_2$, X$_3$ and X$_4$ each, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—R$_8$;

any two or more of the substituents taken together may form a carbocycle or heterocycle ring having from 4 to 8 atoms in the ring structure;

with the proviso that at least one of $R_1$, $Y_1$, $X_1$ and $X_2$ is covalently bonded to at least one of $R_2$, $Y_2$, $X_3$ and $X_4$ to provide the β-alkoxylimines to which they are attached as a tetradentate ligand, and at least one of $Y_1$ and $Y_2$ is a hydrogen;

$R_8$ represents an aryl, a cycloalkyl, a cycloalkenyl, a heterocycle, or a polycycle;

m is zero or an integer in the range of 1 to 8;

M represents the metal; and

A represents a counterion, wherein each of of the substituents $R_1$, $R_2$, $Y_1$, $Y_2$, $X_1$, $X_2$, $X_3$ and $X_4$, are selected such that the catalyst is asymmetric.

For example, a preferred class of catalysts are represented by the general formula:

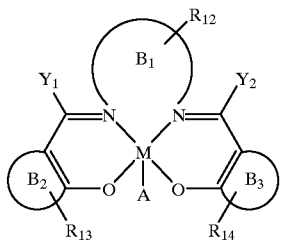

wherein the $B_1$ moiety represents a diimine bridging substituent represented by —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphoryl, a carbonyl, a silyl, an oxygen, a sulfur, a sufonyl, a selenium, a carbonyl, or an ester;

each of $B_2$ and $B_3$ independently represent rings selected from a group consisting of cycloalkyls, cycloakenyls, aryls, and heterocyclic rings, which rings comprising from 4 to 8 atoms in a ring structure;

$Y_1$ and $Y_2$ each independently represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—$R_8$, $R_{12}$, $R_{13}$, and $R_{14}$ each independently are absent, or represent one or more covalent substitutions of $B_1$, $B_2$ and $B_3$ with halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—$R_8$, wherein $R_{12}$ can occur on one or more positions of —$R_{15}$—$R_{16}$—$R_{17}$—, or any two or more of the $R_{12}$, $R_{13}$, $R_{14}$, $Y_1$ and $Y_2$ taken together form a bridging substituent;

$R_8$ represents an aryl, a cycloalkyl, a cycloalkenyl, a heterocycle, or a polycycle;

m is zero or an integer in the range of 1 to 8;

M represents a metal; and

A represents a counterion, wherein $R_{12}$, $R_{13}$, $R_{14}$, $Y_1$ and $Y_2$ are selected such that the catalyst is asymmetric.

In additional preferred embodiments, the catalyst is a metallosalenate catalyst represented by the general formula:

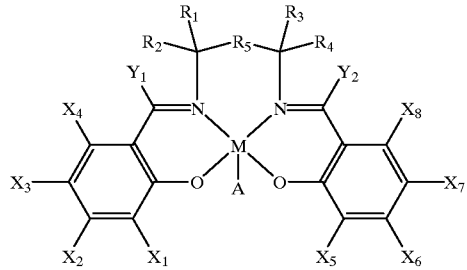

wherein each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—$R_8$;

any two or more of the substituents taken together may form a carbocycle or heterocycle having from 4 to 10 atoms in the ring structure;

$R_8$ represents an aryl, a cycloalkyl, a cycloalkenyl, a heterocycle or a polycycle;

m is zero or an integer in the range of 1 to 8;

M represents a metal; and

A represents a counterion; wherein if $R_5$ is absent, at least one of $R_1$ and $R_2$ taken together with at least one of $R_3$ and $R_4$ forms a bridging substituent, and each of the substituents of 106 are selected such that the salenate is asymmetric.

Alternatively, the catalyst comprises a tridentate ligand, such as the catalyst represented by the general formula:

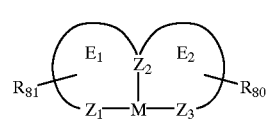

wherein $Z_1$, $Z_2$, and $Z_3$ each represent a Lewis base;

the $E_1$ moiety, taken with $Z_1$, $Z_2$ and M, and the $E_2$ moiety, taken with $Z_2$, $Z_3$ and M, each, independently, form a heterocycle;

$R_{80}$ and $R_{81}$ each independently are absent, hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—$R_8$;

any two or more of the $R_{80}$ and $R_{81}$ substituents taken together may form a bridging substituent;

$R_8$ represents an aryl, a cycloalkyl, a cycloalkenyl, a heterocycle or a polycycle;

m is zero or an integer in the range of 1 to 8;

M represents a metal; and

A represents a counteranion, wherein the tridentate ligand is asymmetric.

In certain embodiments, the catalyst complex comprises a tridentate ligand and is represented by general structure 160:

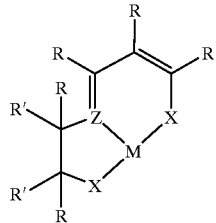

160 wherein

Z represents N, P or As;

X represents independently for each occurrence O, S, Se or ZR;

M represents a metal ion and the requisite number of counterions;

R represents independently for each occurrence hydrogen, alkyl, aryl, halo, acyl or aralkyl; or taken together any two instances of R on adjacent carbons may represent an optionally substituted ring consisting of 3–8 backbone atoms inclusive; said ring being saturated, unsaturated or aromatic; and said ring may be fused to another optionally substituted ring;

R' represents independently for each occurrence hydrogen, alkyl, aryl, halo, acyl or aralkyl; or taken together the two instances of R' may represent an optionally substituted ring consisting of 3–8 backbone atoms inclusive; said ring being saturated, unsaturated or aromatic; and said ring may be fused to another optionally substituted ring; and one or both of the carbons bearing an instance of R' may be asymmetric.

In certain embodiments, the catalyst complex comprises a tridentate ligand and is represented by general structure 162:

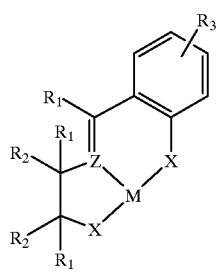

162 wherein

X represents independently for each occurrence O, S, Se or $ZR_1$;

Z represents independently for each occurrence N, P or As;

M represents a metal ion and the requisite number of counterions;

$R_1$ represents independently for each occurrence hydrogen, alkyl or aryl;

$R_2$ represents independently for each occurrence hydrogen, alkyl or aryl; and taken together the two instances of $R_2$ may represent an optionally substituted ring consisting of 3–8 backbone atoms inclusive; said ring being saturated, unsaturated or aromatic; and said ring may be fused to another optionally substituted ring;

$R_3$ may be absent or present between one and four times inclusive;

$R_3$ represents independently for each occurrence alkyl, aryl, aralkyl, halo, acyl, sulfonyl, —$(C(R_1)_2)_m COR_1$, —$(C(R_1)_2)_m CO_2R_1$, —$(C(R_1)_2)_m NO_2$, —$(C(R_1)_2)_m S(O)_n R_1$, —$(C(R_1)_2)_m OR_1$, —$(C(R_1)_2)_m N(R_1)_2$;

n represents independently for each occurrence an integer in the range 0–3 inclusive;

m represents independently for each occurrence an integer in the range 0–8 inclusive; and one or both of the carbons bearing an instance of $R_2$ may be asymmetric.

DETAILED DESCRIPTION OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. The advantages of enantiomerically pure compounds (reviewed in, e.g., Stinson, S. C., *Chem Eng News*, Sept. 28, 1992, pp. 46–79) include fewer side effects and greater potency in many cases. As described herein, the present invention makes available methods and reagents for enantioselective synthesis involving cycloaddition reactions. The primary constituents of the method, set out in more detail below, are a chiral, non-racemic metal catalyst of particular tetradentate or tridentate geometry; a chiral or prochiral diene, and a chiral or prochiral dienophile; the diene and/or dienophile are chosen so that the outcome of the reaction is influenced by the presence of the aforementioned chiral, non-racemic catalyst.

I. Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as amines, mercaptans and alcohols, and charged moieties such as alkoxides, thiolates, carbanions, and a variety of organic and inorganic anions. Illustrative anionic nucleophiles include simple anions such as azide, cyanide, thiocyanate, acetate, formate or chloroformate, and bisulfite. Organometallic reagents such as organocuprates, organozincs, organolithiums, Grignard reagents, enolates, acetylides, and the like may, under approriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "diene" refers to a molecule containing at least one pair of conjugated π-bonds. The individual π-bonds of the diene moiety may be between any two atoms drawn from the set composed of C, N, O, S, and P. The conjugated conjugated π-bonds of the diene must be capable of adopting the so-called s-cis conformation.

The term "dienophile" refers to a molecule containing at least one reactive π-bond. The reactive π-bond of the dienophile may be between any two atoms drawn from the set composed of C, N, O, S, and P. In preferred embodiments, exactly one of the atoms contained in the reactive π-bond is carbon.

The term "ring expansion" refers to a process whereby the number of atoms in a ring of a cyclic compound is increased. An illustrative example of ring expansion is the reaction of epoxides with $CO_2$ to yield cyclic carbonates.

The term "meso compound" is recognized in the art and means a chemical compound which has at least two chiral centers but is achiral due to the presence of an internal plane or point of symmetry.

The term "chiral" refers to molecules which have the property of non-superimposability of their mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoisomerically-enriched" product (e.g., enantiomerically-enriched or diastereomerically-enriched) when the yield of a particular stereoisomer of the product is greater by a statistically significant amount relative to the yield of that stereoisomer resulting from the same reaction run in the absence of a chiral catalyst. For example, a reaction which routinely produces a racemic mixture will, when catalyzed by one of the subject chiral catalysts, yield an e.e. for a particular enantiomer of the product.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant majority of a certain regioisomer.

The term "reaction product" means a compound which results from the reaction of the two substrate molecules. In general, the term "reaction product" will be used herein to refer to a stable, isolable compound, and not to unstable intermediates or transition states.

The term "complex" as used herein and in the claims means a coordination compound formed by the union of one or more electronically rich molecules or atoms capable of independent existence with one or more electronically poor molecules or atoms, each of which is also capable of independent existence.

The term "substrate" is intended to mean a chemical compound which can react under the subject conditions to yield a product having at least one stereogenic center.

The term "catalytic amount" is recognized in the art and means a substoichiometric amount of the catalyst relative to a reactant. As used herein, a catalytic amount means from 0.0001 to 90 mole percent catalyst relative to a reactant, more preferably from 0.001 to 50 mole percent, still more preferably from 0.01 to 10 mole percent, and even more preferably from 0.1 to 5 mole percent catalyst to reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% enantiomeric excess A (ee)=(% enantiomer A)−(% enantiomer B)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a reactant or reactants (which may be achiral, racemic, non-racemic or enantiomerically pure) to a product enriched in one diastereomer. If the chiral reactant is racemic, in the presence of a chiral, non-racemic reagent or catalyst, one reactant enantiomer may react more slowly than the other. This effect is termed a kinetic resolution, wherein the reactant enantiomers are resolved by differential reaction rate to yield an enantiomerically enriched product. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another reactive center. For example, a regioselective cycloaddition reaction of an unsyrmetrical 1,3,5-triene substrate would preferentially occur at one of the two 1,3-dienes contained therein.

The term "non-racemic" means a preparation having greater than 50% of a desired stereoisomer, more preferably at least 75%. "Substantially non-racemic" refers to preparations which have greater than 90% ee for a desired stereoisomer, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, an alkoxyl, a silyloxy, a carbonyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides, phosphoryls (inlcuding phosphonates and phosphines), sulfonyls (inlcuding sulfates and sulfonates), and silyl groups, as well as ethers, thioethers, selenoethers, carbonyls (including ketones, aldehydes, carboxylates, and esters), —$CF_3$, —CN and the like. Exemplary substitued alkyls are described below. Cycloalkyls can be further substituted with alkyls, alkenyls, alkoxys, thioalkyls, aminoalkyls, carbonyl-substituted alkyls, $CF_3$, CN, and the like.

The terms "alkenyl" and "alkynyl" refer to unsaturated aliphatic groups analogous in length and possible substitution to the alkyls described above, but which contain at least one double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

Thus, the term "alkylamine" as used herein means an alkyl group, as defined above, having a substituted or unsubstituted amine attached thereto. In exemplary embodiments, an "amine" can be represented by the general formula:

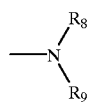

wherein $R_8$ and $R_9$ each independently represent a hydrogen, an alkyl, an alkenyl, —$(CH_2)_m$—$R_7$, —C(=O)-alkyl, —C(=O)-alkenyl, —C(=O)-alkynyl, —C(=O)—$(CH_2)_m$—$R_7$, or $R_8$ and $R_9$ taken together with the N atom to which they are attached complete a heterocycle having from 4 to 8 atoms in the ring structure; $R_7$ represents an aryl, a cycloalkyl, a cycloalkenyl, a heterocycle or a polycycle; and m is zero or an integer in the range of 1 to 8.

Likewise, the term "alkylamide" refers to an alkyl group having a substituted or unsubstituted amide group attached thereto. For instance, an "amide" can be represented by the general formula:

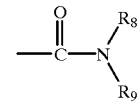

wherein $R_8$ and $R_9$ are as defined above.

The term "alkylimine" refers to an alkyl group having a substituted or unsubstituted imine attached thereto. An "imine" can be represented by the general formula:

wherein $R_8$ is as described above.

The term "thioalkyl" refers to an alkyl group, as defined above, having a sulfhydryl or thioether group attached thereto. In preferred embodiments, the "thioether" moiety is represented by one of —S-alkyl, —S-alkenyl, —S-alkynyl, and —S—$(CH_2)_m$—$R_7$, wherein m and $R_7$ are defined above.

The term "carbonyl-substituted alkyl" as used herein means an alkyl group, as defined above, having a substituted or unsubstituted carbonyl group attached thereto, and includes aldehydes, ketones, carboxylates and esters. In exemplary embodiments, the "carbonyl" moiety is represented by the general formula:

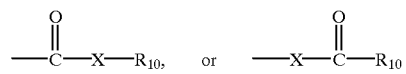

wherein X is absent or represents an oxygen or a sulfur, and $R_{10}$ represents a hydrogen, an alkyl, an alkenyl, or —$(CH_2)_m$—$R_7$, where m and $R_7$ are as defined above. Where X is an oxygen, the formula represents an "ester". Where X is a sulfur, the formula represents a "thioester." Where X is absent, and $R_{10}$ is not hydrogen, the above formula represents a "ketone" group. Where the oxygen atom of the above formula is replaced by sulfur, the formula represents a "thiocarbonyl" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl which renders that alkyl an ether is or resembles an alkoxyl, such as can be represented by one of —O-alkyl, —O-alkenyl, —O-alkynyl, —O—$(CH_2)_m$—$R_7$, where m and $R_7$ are described above.

Thus, the term "phosphorylalkyl" as used herein means an alkyl group, as defined above, having a substituted or unsubstituted phosphoryl group attached thereto. A "phosphoryl" can in general be represented by the formula:

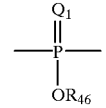

wherein $Q_1$ represented S or O, and $R_{46}$ represents hydrogen, a lower alkyl or an aryl. When used to substitute an alkyl, the phosphoryl group of the phosphorylalkyl can be represented by the general formula:

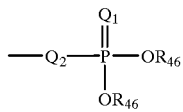

wherein $Q_1$ represented S or O, and each $R_{46}$ indepedently represents hydrogen, a lower alkyl or an aryl, $Q_2$ represents O, S or N.

The term "metalloalkyl" refers to an alkyl group, as defined above, having a substituted or unsubstituted organometallic group attached thereto. A "silyl alkyl" is an alkyl having a substituted silicon attached thereto. In a preferred embodiment, the "silyl" moiety which may be substituted on the alkyl can be represented by the general formula:

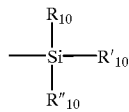

wherein $R_{10}$, $R'_{10}$ and $R''_{10}$ independently represent a hydrogen, an alkyl, an alkenyl, or —$(CH_2)_m$—$R_7$, m and $R_7$ being defined above.

Likewise, a "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

The term "sulfonate" as used herein means a sulfonyl group, as defined above, attached to an alkyl or aryl group. Thus, in a preferred embodiment, a sulfonate has the structure:

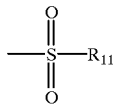

in which $R_{11}$ is an alkyl or an aryl.

The term sulfate, as used herein, means a sulfonyl group, as defined above, attached to a hydroxy or alkoxy group. Thus, in a preferred embodiment, a sulfate has the structure:

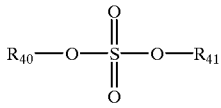

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

A "bridging substituent" refers to a substitution at two (or more) sites on the core structure of the catalyst by the same (as opposed to identical) substituent so as to form a covalent bridge between the substitution sites. For example, a bridging substituent may be represented by the general formula or —$R_{15}$—$R_{16}$—$R_{17}$—, wherein $R_{15}$ and $R_{17}$ each independently are absent or represent an alkyl, an alkenyl, or an alkynyl, preferably $C_1$ to $C_{10}$, and $R_{16}$ is absent or represents an amine, an imine, an amide, a phosphoryl a carbonyl, a silyl, an oxygen, a sulfonyl, a sulfer, a selenium, or an ester. Exemplary bridging substituents are given by the "picnic basket" forms of, for instance, the porphoryn catalysts described below.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

II. Catalyzed Reactions

In one aspect of the present invention there is provided a process for stereoselectively producing compounds with at least one stereogenic center. An advantage of this invention is that enantiomerically enriched products can be synthesized from achiral or racemic reactants. Another advantage is that yield losses associated with the production of an undesired enantiomer can be substantially reduced.

In general, the invention features a stereoselective cycloaddition process which comprises combining a diene, a dienophile, and at least a catalytic amount of a non-racemic, chiral catalyst of particular characteristics (as described below). The combination is maintained under conditions appropriate for the chiral catalyst to catalyze a stereoselective cycloaddition between the diene and dienophile. This reaction can be applied to enatioselective processes as well as diastereoselective processes. It may also be adapted for regioselective reactions. Examples of enantioselective reactions, kinetic resolution, and regioselective reactions which may be catalyzed according to the present invention follow.

In an exemplary embodiment, a Hetero-Diels-Alder reaction between an aldehyde and an electron-rich diene in the presence of a subject chiral, non-racemic catalyst yields a non-racemic dihydropyran product. This embodiment is an example of a diastereo- and enantioselective cycloaddition reaction.

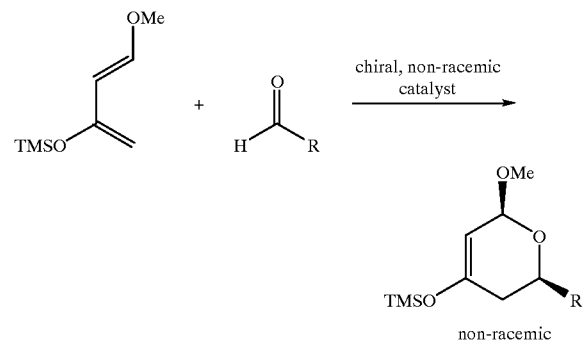

In another aspect of the invention, the hetero-Diels-Alder reaction occurs in a regioselective manner in the presence of a chiral, non-racemic catalyst. An illustrative example of a regioselective reaction is shown below. This exemplary embodiment of the subject invention involves diastereo-, regio- and enantioselective Hetero-Diels-Alder reactions exemplified by the thiene synthesis below.

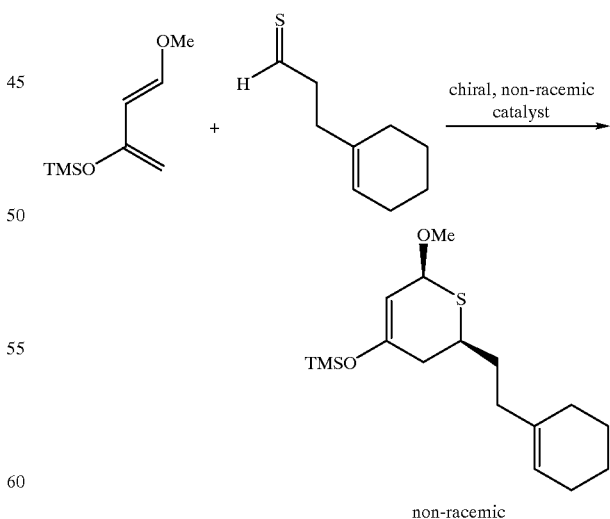

As shown below, the present invention also provides a method for stereoselective type 1 and type 2 intramolecular Hetero-Diels-Alder reactions.

Type 1 Intramolecular Hetero-Diels-Alder Reaction

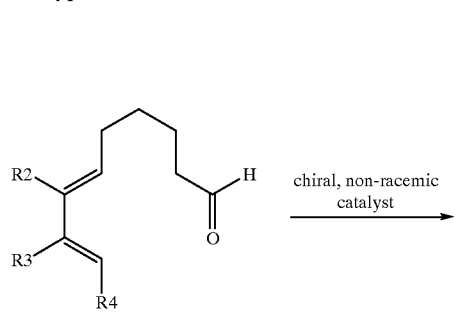

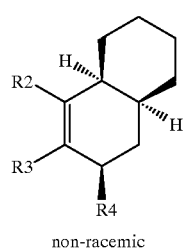

non-racemic

Type 2 Intramolecular Hetero-Diels-Alder Reaction

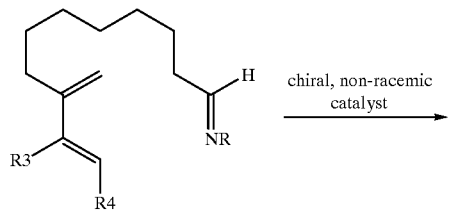

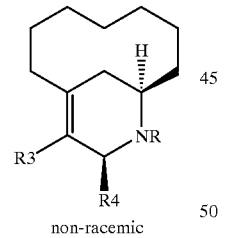

non-racemic

In another illustrative embodiment, the present invention provides a method for the kinetic resolution of a racemic mixture of an aldehyde containing an α-stereocenter. In the subject metal-mediated kinetic resolution process of a racemic aldehyde substrate, one enantiomer of the aldehyde can be recovered as unreacted substrate while the other is transformed to the desired product. This aspect of the invention provides methods of easily synthesizing functionalized non-racemic products from racemic starting materials.

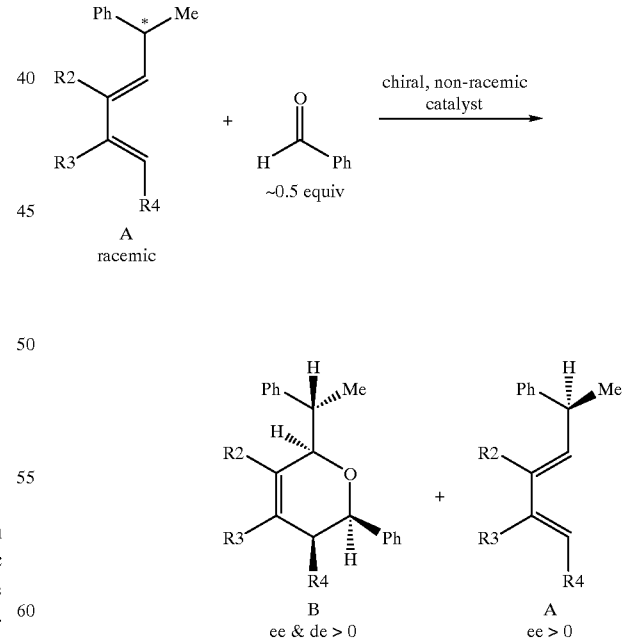

A second facet of kinetic resolution possible with the subject method involves resolution of a racemic diene substrate. In a preferred embodiment, racemic diene A will react with substoichiometric benzaldehyde (~0.5 equiv) in the presence of a subject chiral, non-racemic catalyst to yield dihydropyran B (de and ee>0) and unreacted A (ee>0). This type of kinetic resolution is rationalized by a presumed difference in the energies of the diastereomeric transition states for the reaction between the individual enantiomers of racemic A, and the chiral, non-racemic complex comprising benzaldehyde and the catalyst. This rationalization is not intended to be limiting in any way.

As skilled artisans will recognize readily, the subject invention can be applied to 1,3-dienes which incorporate heteroatoms in their diene backbones. In a preferred embodiment, the 2-aza-1,3-diene shown below will react with acetaldehyde in the presence of a subject catalyst to provide stereoselectively the heterocyclic product.

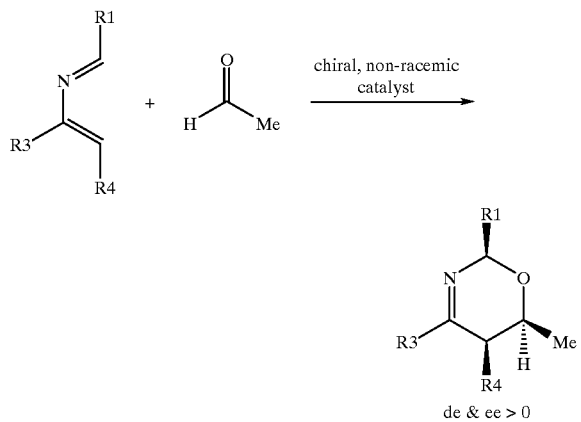

The overall reaction of an aldehyde with a 1,3-diene to generate a dihydropyran—the "classical" diene-aldehyde cyclocondensation reaction—has been shown to proceed via a stepwise, rather than a concerted, mechanism in certain cases (refer to the articles by Corey and Keck cited earlier for relevant examples and a discussion of this issue). Based on this literature, a preferred embodiment of the present invention involves the use of the instant chiral, non-racemic catalysts for the asymmetric aldol condensation of an aldehyde and a silyl enol ether. In additional prefered embodiments, the aldehyde substrate for these so-called "Mukaiyama" aldol condensations may be replaced with any carbonyl-containing compound including, but not limited to, ketones, esters, amides, imines and the like.

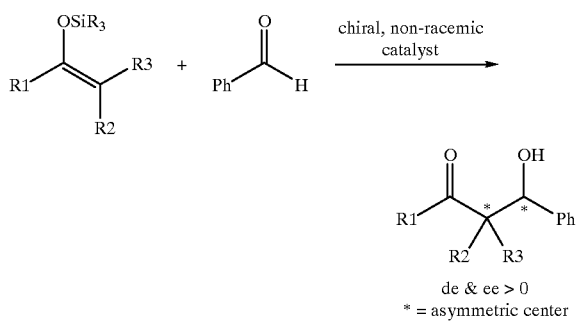

The processes of this invention can provide optically active products with very high stereoselectivity (e.g., enantioselectivity or diasteroselectivity) or regioselectivity. In preferred embodiments of the subject enantioselective reactions, enantiomeric excesses of preferably greater than 50%, more preferably greater than 75% and most preferably greater than 90% can be obtained by the processes of this invention. Likewise, with respect to regioselective reactions, molar ratios for desired/undesired regioisomers of preferably greater than 5:1, more preferably greater than 10:1 and most preferably greater than 25:1 can be obtained by the processes of this invention. The processes of this invention can also be carried out at highly desirable reaction rates suitable for commercial use.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include epoxidation, ozonolysis, halogenation, hydrohalogenation, hydrogenation, esterification, oxidation of alcohols to aldehydes, ketones and/or carboxylate derivatives, N-alkylation of amides, addition of aldehydes to amides, nitrile reduction, acylation of alcohols by esters, acylation of amines and the like. To further illustrate, exemplary classes of pharmaceuticals which can be synthesized by a scheme including the subject stereoselective reaction are cardiovascular drugs, non-steroidal antiinflammatory drugs, central nervous system agents, and antihistaminics.

III. Catalysts

The catalysts employed in the subject method involve chiral complexes which provide controlled steric environments for asymmetric cycloadditon reactions. In general, catalysts intended by the present invention can be characterized in terms of a number of features. For instance, a salient aspect of each of the catalysts contemplated by the instant invention concerns the use of metalloligands which provide a rigid or semi-rigid environment near the catalytic site of the molecule. This feature, through imposition of structural rigidity on the chelated metal, can be used to establish selective approach of the substrate to the catalytic site and thereby induce stereoselectivity and/or regioselectivity in a cycloaddition reaction. Moreover, the ligand preferably places a restriction on the coordination sphere of the metal.

Another aspect of the catalyst concerns the selection of metal atoms for the catalyst. In general, any Lewis acidic metal may be used to form the catalyst, e.g., a main group metal, a metal selected from one of Groups 3–12 of the periodic table, or from the lanthanide series. In certain embodiments, the metal is a main group metal selected from the group consisting of Al, Ga, In, Si, Ge, and Sn. However, in preferred embodiments, the metal will be selected from the group of late transition metals, e.g. preferably from Groups 5–12, in order to provide metal centers which are coordinatively unsaturated and not in their highest oxidation state. For example, suitable metals include Co, Cr, Mn, V, Fe, Mo, W, Ru and Ni. Particularly preferred metals are from group 6, especially Cr(III).

A. Chiral Tetradentate Catalysts

Consistent with these desirable features, one class of particularly preferred chiral catalysts provide a chiral tetradentate ligand which coordinates a metal in a substantially square planar or square pyramidal geometry, though some distortion to these geometries is contemplated. Restated, these square geometries refer to tetradentate ligands in which the Lewis basic atoms lie substantially in the same plane, with the metal also in that plane (square planar), or above or below that plane (square pyramidal).

Preferred square tetradentate catalysts which may be employed in the subject reactions can be represented by the general formula 100:

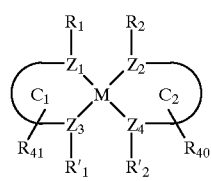

wherein $Z_1$, $Z_2$, $Z_3$ and $Z_4$ each represent a Lewis base, such as selected from the group consisting of nitrogen (e.g., imines, amines and amides), oxygen, phosphorus (e.g., phosphines or phosphinites), arsenic (arsines) and sulfur.

The $C_1$ moiety (taken with $Z_1$, $Z_3$ and M) and the $C_2$ moiety, (taken with $Z_2$, $Z_4$ and M) each, independently, form a heterocyclic ring. It will be understood that while the $C_1$ and $C_2$ structures depicted in the above formula may not formally be covalently closed rings for lack of a covalent bond with the metal M, for purposes of this disclosure, this and similar structures involving the metal catalyst atom M will nevertheless be referred to as heterocyclic rings, and substituents thereof will be referenced relative to heterocycle nomenclature (e.g., "fused rings" or "bridged rings"). In addition to substitutions at $R_1$, $R_2$, $R'_1$ and $R'_2$, the $C_1$ and $C_2$ rings can of course be substituted as appropriate at other ring positions, as illustrated by $R_{40}$ and $R_{41}$. Moreover, it will be appreciated that in certain embodiments two or more substituents of $C_1$ can be covalently bonded to each other to provide a fused ring or bridged ring including the $C_1$ ring atoms. Similar structures can be provided on the $C_2$ ring.

Accordingly, in the illustrated structure 100, $R_1$, $R_2$, $R'_1$ and $R'_2$ each independently are absent, or represent some substitution, as permitted by valence requirements, of the Lewis basic atoms, which substitution may be with hydrogen, halogens, alkyls, alkenyls, alkynyls, hydroxyl, alkoxyl, silyloxy, amino, nitro, thio amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ substituents taken together can form a bridging substituent; with the proviso that at least one of $R_1$, $R'_1$ and $R_{41}$ forms a bridging substituent with at least one of $R_2$, $R'_2$ and $R_{40}$ in order to provide $C_1$ and $C_2$ as a tetradentate; $R_7$ represents an aryl, a cycloalkyl, a cycloalkenyl, a heterocycle or a polycycle, and m is zero or an integer in the range of 1 to 8.

While the actual substituents of $C_1$ and $C_2$ can vary widely as necessary for a particular reaction scheme, one important proviso is that at least one substituent of $C_1$ must form a covalent bond with at least one substituent of $C_2$ in order to provide a tetradentate ligand which forms a square complex with M. That is, the ligand is a bridged cycle or polycycle which includes $C_1$ and $C_2$. Furthermore, in order for the catalyst to be chiral, e.g., to be capable of catalyzing stereoselective reactions, $R_1$, $R_2$, $R'_1$, $R'_2$ and other substituents of $C_1$ and $C_2$ are selected to provide at least one stereogenic center or an axis of dissymmetry, e.g. such that the ligand is asymmetric.

In the general structure 100, M represents a main group metal, a transition metal of Group 3–12 or the lanthide series of the periodic table, though preferably a metal ion which is not in its highest oxidation state. In the most preferred embodiments, M will be selected from the group of late transition metals,e.g., from the Group 5–12 metals. Even more preferably, M will be Cr(III). Moreover, the metal can be coordinated with a counteranion (as in the aged catalyst described below).

Exemplary catalysts of this class are comprised of ligands derived from, for example, salens, porphyrins, crown ethers, azacrown ethers, cyclams, phthalocyanines, and the like.

In a particularly preferred embodiment, the subject reactions use a chiral catalyst having a metal ion complexed via an imine of a chiral ligand, preferably a diimine bridge. Accordingly, such variants of structure 100 can be provided in embodiments wherein any one or more of the Lewis bases is an imine, with metallo-Schiff base forms of imines being highly preferred.

To further illustrate, a tetradentate catalyst useful in the subject method can be derived using chiral salen or salen-like ligands (hereinafter "salenates"). The asymmetric metallosalenate catalysts offer a distinct advantage over many other chiral tetradentate catalyts, such as the metalloporphyrinates described infra, in that the salenate ligand can have stereogenic centers located just two bond lengths away from the metal. This proximity of the chiral centers to the reactive site can yield a high degree of stereoselectivity.

As disclosed herein, salen complexes are highly effective catalysts for the asymmetric hetero-Diels-Alder reaction and other cycloaddition reactions. This group of reactions is notable not only for its high enantioselectivity and for the utility of its products, but also for its remarkable efficiency as a catalytic process.

Moreover, the synthesis of chiral salenates is well characterized in the art, with more than 150 different chiral metallosalenates having been reported in the literature (see, for review, Collman et al. (1993) *Science* 261:1404–1411). These ligands are easily and inexpensively synthesized on large scale starting from readily available materials, as described in Larrow et al., *J. Org Chem* (1994) 59:1939–1942. Importantly, the general familiarity and ease of synthesis of metallosalenates permits the substituents to be readily varied in a systematic fashion in order to adjust the steric or electronic characteristics of the ligand. This feature makes possible the synthesis of ligands which are optimized for particular types of reaction or substrate. It has been found that such steric and electronic "tuning" (described infra) can have significant effects on the yield and e.e. of products formed in asymmetric reactions. In particular, the use of bulky blocking substituents is desirable to achieve high product e.e. in the asymmetric cycloadditions. Furthermore, the stereogenic moiety can easily be modified to improve enantioselectivity.

In general, the salenate ligands which are useful in the subject method as chiral metallosalenate catalysts can be characterized as two substituted β-alkoxylimines which are linked to form a tetradentate ligand having at least one stereogenic center. In an exemplary embodiment, a metallosalenate catalyst useful in the asymmetric cycloaddition processes of the present invention can be represented by a metal complex with two substituted β-alkoxylimines having the general formula:

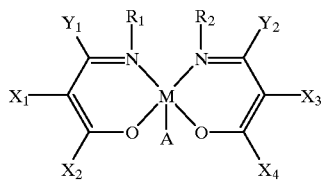

wherein
- the substituents $R_1$, $R_2$, $Y_1$, $Y_2$, $I_1$, $X_2$, $X_3$ and $X_4$ each, independently, represent hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$,
- or any two or more of the substituents taken together form a carbocycle or heterocycle having from 4 to 8 atoms in the ring structure, which ring structure may be a fused ring, as in the case of, for example, $X_1$ and $X_2$ forming a ring, or which ring may be a bridging ring, as in the case of $R_1$ and $R_2$, $X_2$ and $X_4$, or $Y_1$ and $X_2$ representing different ends of a single substituent,
- with the proviso that at least one of $R_1$, $Y_1$, $X_1$ and $X_2$ is covalently bonded to at least one of $R_2$, $Y_2$, $X_3$ and $X_4$ to provide the β-alkoxylimines as a tetradentate ligand;
- $R_7$ represents an aryl, a cycloalkyl, a cycloalkenyl, a heterocycle, or a polycycle;
- m is zero or an integer in the range of 1 to 8;
- M represents a metal; and
- A represents a counterion;

wherein each of of the substituents of the β-alkoxylimines, e.g., $R_1$, $R_2$, $Y_1$, $Y_2$, $X_1$, $X_2$, $X_3$ and $X_4$, are selected such that the catalyst is asymmetric.

The choice of each of $R_1$, $R_2$, $Y_1$, $Y_2$, $X_1$, $X_2$, $X_3$ and $X_4$ is also dependent on electronic and steric considerations, e.g., the tuning of the catalyst for a particular set of substrates, as well as the solvent system in which the reaction is to be carried out.

The chirality of the salenate ligand may be the result of the presence of one or more chiral atoms (e.g. carbon, sulfur, phosphorus, or other atoms capable of chirality), or may be the result of restricted rotation, helicity, molecular knotting or chiral metal complexation. In preferred embodiments, the chiral ligand has at least one chiral atom or is asymmetric due to restricted rotation. Further guidance regarding the particular choice of the substituents is set out herein.

In preferred embodiments, the choice of $R_1$, $R_2$, $X_1$, $X_2$, $X_3$ and $X_4$ yield a class of chiral catalysts which are represented by the general formula:

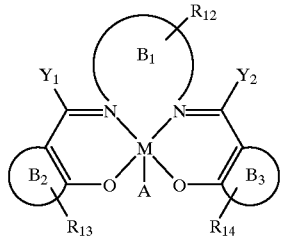

in which the $B_1$ moiety represents a diimine bridge, e.g. a bridging substituent which links the imino nitrogens of each β-alkoxylimine, and preferably contains at least one chiral center of the salen ligand. For example, $B_1$, taken together with the metal-coordinating imines of the β-alkoxylimine, can represent the diimine of an alkyl, an alkenyl, an alkynyl, or the diimine of —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfur, a sulfonyl, a selenium, or an ester; each of $B_2$ and $B_3$ independently represent rings selected from a group consisting of cycloalkyls, cycloalkenyls, aryls, and heterocycles, which rings comprise from 4 to 8 atoms in a ring structure. The substituents $R_{12}$, $R_{13}$ and $R_{14}$ each independently are absent, or represent one or more covalent substitutions of $B_1$, $B_2$ and $B_3$ with halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$ (the substituent $R_{12}$ occuring on one or more positions of —$R_{15}$—$R_{16}$—$R_{17}$—); $R_7$ represents an aryl, a cycloalkyl, a cycloalkenyl, a heterocycle, or a polycycle; m is zero or an integer in the range of 1 to 8. Moreover, any two or more of the $R_{12}$, $R_{13}$, $R_{14}$, $Y_1$ and $Y_2$ substituted taken together can form bridging substituents to bridge the two β-alkoxylimines and/or bridge different portions of the same β-alkoxylimine. As above, in order to provide for a chiral catalyst, the choice of $B_2$ and $B_3$ (including their substituents) and/or the choice of substituents on $B_1$ (e.g., $B_1$ has a stereogenic center) is made to establish a chiral ligand. A represents a counterion.

In particular, as described in the appended examples, the salenate ligand can be derived from condensation of a substituted salicylaldehyde with a substituted diamine, preferably one stereoisomer of a chiral diamine, and then reacted with a desired metal to form a salen (N,N'-bis(salicylideneamino)alkyl) metal complex. An exemplary reaction for generating the salen ligand is based on Zhang and Jacobsen (1991) *J. Org Chem* 56:2296–2298, and Jacobsen et al. PCT WO93/03838, and comprises:

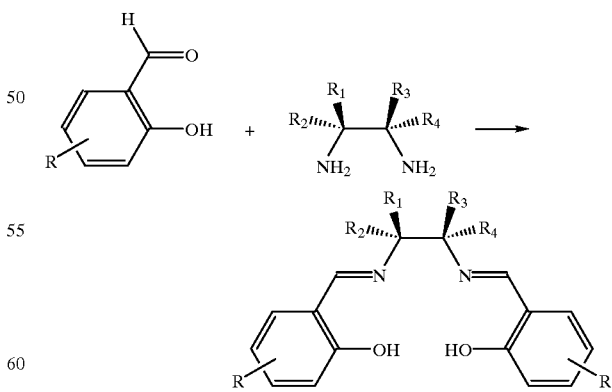

Utilizing this and other reaction schemes generally known in the art can provide a class of salens represented by the general formula:

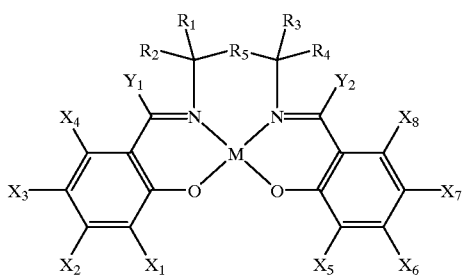

wherein each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, alkoxyl, silyloxy, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

any two or more of the substituents taken together may form a carbocyle or heterocycle having at least 4 atoms in the ring structure;

$R_7$ represents an aryl, a cycloalkyl, a cycloalkenyl, a heterocycle or a polycycle;

m is zero or an integer in the range of 1 to 8; and

M represents a metal;

wherein if $R_5$ is absent, at least one of $R_1$ and $R_2$ is covalently bonded to at least one of $R_3$ and $R_4$; and the substituents of the salenate ligand are selected such that the salenate has at least one stereogenic center, e.g., is asymmetric. Moreover, the metal can be coordinated with a counterion (as in the aged catalyst described below).

With respect to generating a chiral ligand, it is important to note when selecting particular substituents that the salenate ligand has a potential catalytic site on both "sides" of the catalyst, e.g., relative to the plane of the four coordinating atoms of the ligand. Accordingly, when selecting the appropriate substituents for the β-alkoxylimines in the above embodiments, it is important that either (1) both sides of the catalyst have stereogenic centers which effect identical stereoselectivity, or (2) the side having a stereogenic center of appropriate stereoselectivity is accessible while the other side has a blocking structure which substantially impairs approach to the metal atom on that side.

The first of these options is preferred. In other words, it is preferred to have at least one stereogenic center on each side of the salenate ligand, each having the same R/S configuration. For example, (R,R)-1,2-Diphenyl-1,2-bis(3-tert-butylsalicylideamino)ethane, described in the Examples, contains two stereogenic centers on the diimine bridge which give rise to identical stereoselective faces on each side of the catalyst. This bis-faced catalyst has the advantage of not being susceptible to "leakage" reactions because substrate approach, albeit constrained, may occur from either face without loss of selectivity.

In contrast, control of the reactivity of the mono-faced catalyst can be accomplished by sterically hindering substrate approach to the undesired face. For instance, the salenate (R)-2-phenyl-1,2-bis(3-tert-butylsalicylideamino)ethane, e.g., formula 106 wherein $R_1$, $R_2$ and $R_3$ are protons, and $R_4$ is a phenyl, has two non-equivalent faces in terms of enantioselectivity. Accordingly, derivatizing the salenate ligand with a group which blocks access to the "free" face (e.g., the face having both a C1 and C2 proton of the diimine) can establish the ligand as a chiral catalyst with one enantiotopic face. For instance, a "picnic basket" form of the ligand can be generated wherein the phenyl moiety of the diimine bridge is on the "frontside" of the catalyst, and $X_4$ and $X_8$ are covalently linked to form a bridge on the "backside" of the catalyst, which bridge substitution precludes access to the metal ion from the backside. Those skilled in the art will recognize other single- and double-sided embodiments (see, for example, Collman et al. (1993) Science 261:1404).

The synthesis schemes for metallosalenates which may be useful in the present method, or precursors thereof, can be adapted from the literature. For example, see Zhang et al. (1990) J Am Chem Soc 112:2801; Zhang et al. (1991) J. Org Chem 56:2296; Jacobsen et al. (1991) J. Am Chem Soc 113:7063; Jacobsen et al. (1991) J. Am Chem Soc 113:6703; Lee et al. (1991) Tetrahedron Lett 32:5055; Jacobsen, E. N. In Catalytic Asymmetric Synthesis, Ojima, I., Ed., VCH: New York, 1993, chapter 4.2; E. N. Jacobsen PCT Publications WO81/14694 and WO93/03838; Larrow et al. (1994) J. Am Chem Soc 116:12129; Larrow et al. (1994) J. Org Chem 59:1939; Irie et al. (1990) Tetrahedron Lett 31:7345; Irie et al. (1991) Synlett 265; Irie et al. (1991) Tetrahedron Lett 32:1056; Irie et al. (1991) Tetrahedron Asymmetry 2:481; Katsuki et al. U.S. Pat. No. 5,352,814; Collman et al. (1993) Science 261:1404; Sasaki et al. (1994) Tetrahedron 50:11827; Palucki et al. (1992) Tetrahedron Lett 33:7111; and Srinivasan et al. (1986) J. Am Chem Soc 108:2309. Exemplary salenate ligands described in the above references are illustrated below, as well as in the appended examples [Ph=phenyl; tBu=tert-butyl].

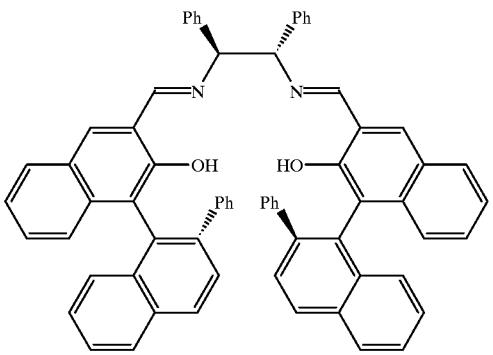

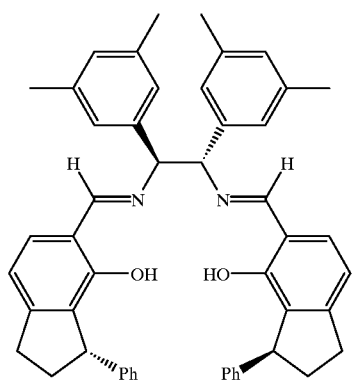

-continued

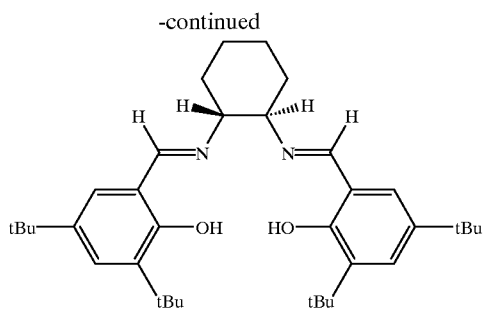

In yet another embodiment of the subject method, the tetradentate catalyst of formula 100 is derived as a chiral tetradentate ligand represented, with the metal atom, by the general formula:

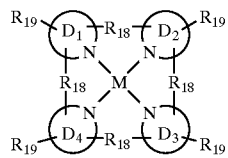

108 in which
- $D_1$, $D_2$, $D_3$ and $D_4$ each represent heterocycles, such as pyrrole, pyrrolidine, pyridine, piperidine, imidazole, pyrazine, or the like;
- each $R_{18}$ occurring in the structure represents a bridging substituent which links adjacent heterocycles, and preferably contains at least one stereogenic center of the ligand. For example, each $R_{18}$, represents an alkyl, an alkenyl, an alkynyl, or $-R_{15}-R_{16}-R_{17}-$, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfonyl, a sulfer, a selenium, or an ester;
- each $R_{19}$, independently, is absent or represents one or more substituents of the heterocycle to which it is attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, and $-(CH_2)_m-R_7$;
- any two or more of the $R_{18}$ and $R_{19}$ substituents may be covalently linked to form a bridge substitution;
- $R_7$ represents an aryl, a cycloalkyl, a cycloalkenyl, a heterocycle or a polycycle;
- m is zero or an integer in the range of 1 to 8; and
- M represents a metal, wherein each of the substituents $R_{18}$ and $R_{19}$ are selected such that the catalyst is asymmetric, e.g., the catalyst contains at least one stereogenic center. The metal will generally be coordinated with a counterion (as in the aged catalyst described below).

In preferred embodiments, $D_1-D_4$ are substituted pyrroles, and the catalyst is a chiral porphyrin or porphyrin-like ligand (hereinafter "porphyrinates"). As with the salenate ligands above, the synthesis of a vast number of porphyrinates has been reported in the literature. In general, most chiral porphyrins have been prepared in three ways. The most common approach involves attaching chiral units to preformed porphyrins such as amino- or hydroxy-substituted porphyrin derivatives (Groves et al. (1983) *J. Am Chem Soc* 105:5791). Alternatively, chiral substituents can be introduced at the porphyrin-forming stage by allowing chiral aldehydes to condense with pyrrole (O'Malley et al. (1989) *J. Am Chem Soc* 111:9116). Chiral porphyrins can also be prepared without the attachment of chiral groups. Similar to the bridged enantiotopic faces described for the salenates above, bridged porphyrinates can be generated by cross-linking adjacent and/or opposite pyrrolic positions and then separating the resulting mono-faced enantiomers with preparative HPLC using a chiral stationary phase (Konishi et al. (1992) *J. Am Chem Soc* 114:1313). Ultimately, as with the generation of chiral salenate ligands, the resulting porphyrinate must have no mirror plane in order to be considered chiral.

With reference to formula 100, it will be understood that metalloporphyrinate catalysts, in addition to being represented by formula 108, can be represented generally by the compound of formula 100 when each of $Z_1$, $Z_2$, $Z_3$ and $Z_4$ represent nitrogen, and $C_1$ and $C_2$ along with their substituents (including $R_1$, $R'_1$, $R_2$, $R'_2$) form four substituted pyrrole rings which include $Z_1$, $Z_2$, $Z_3$ and $Z_4$. To complete the square tetradentate ligand, each pyrrole ring is covalently attached to the two adjacent pyrrole rings.

In preferred embodiments, the metalloporphyrinate catalyst is represented by the general formula:

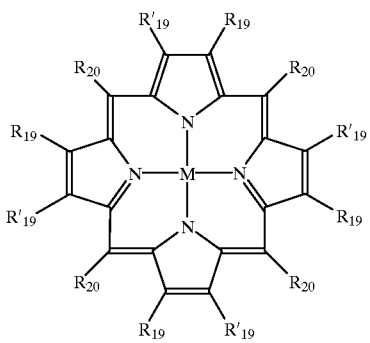

110 in which
- each $R_{20}$ occurring in structure 110, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or $-(CH_2)_m-R_7$;
- each $R_{19}$ and $R'_{19}$ occurring in structure 110, independently, represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or $-(CH_2)_m-R_7$;
- any two $R_{19}$ and $R'_{19}$ substituents on the same pyrrole taken together may form a fused carbocycle or fused heterocycle having from 4 to 7 atoms in the ring structure;
- any two or more of the $R_{19}$, $R'_{19}$ and $R_{20}$ substituents may be covalently cross-linked to form a bridging substituent;

$R_7$ represents an aryl, a cycloalkyl, a cycloalkenyl a heterocycle or a polycycle;

m is zero or an integer in the range of 1 to 8; and

M represents a metal, wherein the substituents $R_{19}$, $R'_{19}$ and $R_{20}$ are selected such that the catalysthas at least one stereogenic center, e.g., is asymmetric. The metal will generally be coordinated with a counterion (as in the aged catalyst described below).

As with the salenate ligands previously described, it is possible to sterically and electronically "tune" the porphyrin ligands to optimize reaction yield and e.e. Examples of suitable porphyrin ligands and synthesis schemes can be adapted from the art. For example, see Chang et al. (1979) *J. Am Chem Soc* 101:3413; Groves et al. (1989) *J. Am Chem Soc* 111:8537; Groves et al. (1990) *J. Org Chem* 55:3628; Mansuy et al. (1985) *J Chem Soc Chem Commun* p155; Nauta et al. (1991) *J. Am Chem Soc* 113:6865; Collman et al. (1993) *J. Am Chem Soc* 115:3834; and Kruper et al. (1995) *J. Org Chem* 60:725.

Still another class of the tetradentate catalysts represented by the general formula 100 and which are useful in the present asymmetric synthesis reactions can be represented by the formula:

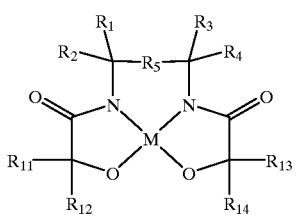

112 wherein each of the substituents $R_1$, $R_2$, $R_3$, $R_4$, $R_5$, $R_{11}$, $R_{12}$, $R_{13}$ and $R_{14}$, independent represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

any two or more of the substituents taken together may form a carbocycle or heterocycle having at least 4 atoms in the ring structure;

$R_7$ represents an aryl, a cycloalkyl, a cycloalkenyl, a heterocycle or a polycycle;

m is zero or an integer in the range of 1 to 8; and

M represents a metal;

wherein if $R_5$ is absent, at least one of $R_1$ and $R_2$ is covalently bonded to at least one of $R_3$ and $R_4$, and the substituents are selected such that the catalyst is asymmetric. The metal will generally be coordinated with a counterion (as in the aged catalyst described below).

Exemplary catalysts of formula 112 include:

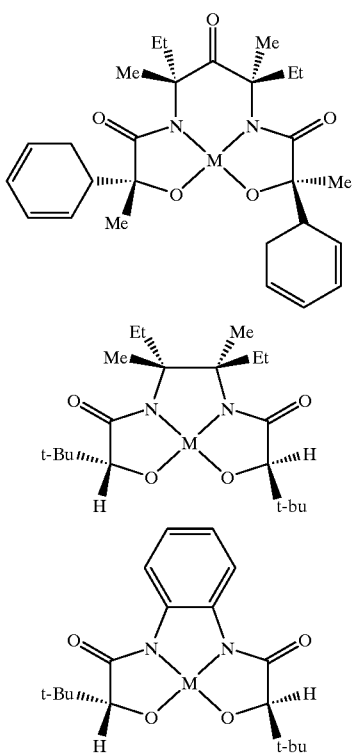

The synthesis of these and other related catalyst can be adapted from the literature. See, for example, Ozaki et al. (1990) *J Chem Soc Perkin Trans*2:353; Collins et al. (1986) *J. Am Chem Soc* 108:2088; and Brewer et al. (1988) *J. Am Chem Soc* 110:423.

In yet another embodiment, the tetradentate catalysts of formula 100 can be chosen from the class of azamacrocycle having a ligand represented by the general formula:

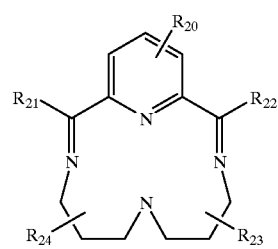

114 wherein $R_{21}$ and $R_{22}$ each represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{20}$ is absent or represents one or more substituents of the pyridine to which it is attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

$R_{23}$ and $R_{24}$ each independently are absent or represent one or more substituents of the 1,3-diiminopropyl to which they are attached, each substituent independently selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the $R_{20}$, $R_{21}$, $R_{22}$, $R_{23}$ and $R_{24}$ substituents are covalently linked to form a bridging substituent;

$R_7$ represents an aryl, a cycloalkyl, a cycloalkenyl, a heterocycle or a polycycle; and m is zero or an integer in the range of 1 to 8, wherein the substituents $R_{20}$, $R_{21}$, $R_{22}$, $R_{23}$ and $R_{24}$ are selected such that the catalyst is asymmetric.

One advantage to this class of tetradentate catalysts, like the salenates, derives from the fact that the ligand provides a metallo-shiff base complex. Furthermore, stereogenic centers can be sited within two bond lengths of the metal center. Exemplary ligands of formula 114 include:

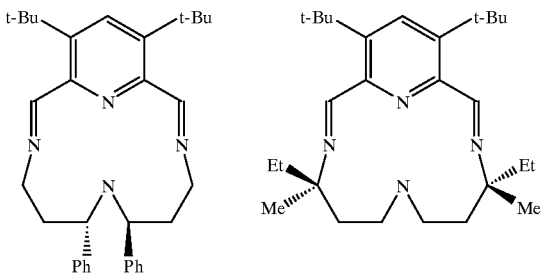

The synthesis of these and other embodiments of 114 are described in Prince et al. (1974) *Inorg Chim Acta* 9:51–54, and references cited therein.

Yet another class of tetradentate ligands of the subject method are the cyclams, such as represented by the general formula:

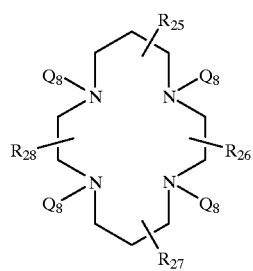

116 in which each of the substituents $Q_8$ indpendently, are absent or represent hydrogen or a lower alkyl, and each of $R_{25}$, $R_{26}$, $R_{27}$ and $R_{28}$, independently, represent one or more substituents on the ethyl or propyl diimine to which they are attached, which substituents are selected from the group of hydrogen, halogens, alkyls, alkenyls, alkynyls, hydroxyl, alkoxyl, silyloxy, amino, nitro, thiol, amines, imines, amides, phosphonates, phosphines, carbonyls, carboxyls, silyls, ethers, thioethers, sulfonyls, selenoethers, ketones, aldehydes, esters, and —$(CH_2)_m$—$R_7$; or any two or more of the substituents taken together form a bridging substituent; $R_7$ represents an aryl, a cycloalkyl, a cycloalkenyl, a heterocycle, or a polycycle; and m is zero or an integer in the range of 1 to 8. Wherein the substituents are selected such that the catalyst is asymmetric. Exemplary embodiments and synthesis schemes for chiral cyclams useful in the present invention can be adapted from the art. See, for example, the Burrows et al. U.S. Pat. No. 5,126,464, Kimura et al. (1984) *Inorg Chem* 23:4181; Kimura et al. (1984) *J. Am Chem Soc* 106: 5497; Kushi et al. (1985) *J Chem Soc Chem Commun* 216; Machida et al. (1986) *Inorg Chem* 25:3461; Kimura et al. (1988) *J. Am Chem Soc* 110:3679; and Tabushi et al. (1977) *Tetrahedron Lett* 18:1049.

B. Chiral Tridentate Catalysts

In yet another embodiment of the subject method, the chiral catalyst which is provided in the reaction is from a class of chiral catalyst having a tridentate ligand which coordinates a transition metal in a substantially planar geometry, though as above some distortion to this geometry is contemplated. Accordingly, this planar geometry refers to tridentate ligands in which the Lewis basic atoms lie substantially in the same plane, with the metal also in that plane, or slightly above or below that plane.

Preferred planar tridentate catalysts which may be employed in the subject reactions can be represented by the general formula 140:

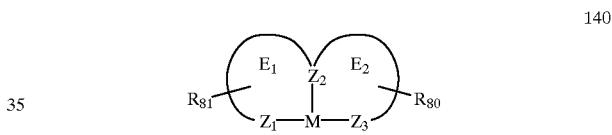

140 wherein $Z_1$, $Z_2$, and $Z_3$ each represent a Lewis base, such as selected from the group consisting of nitrogen, oxygen, phosphorus, arsenic and sulfur; the $E_1$ moiety, taken with $Z_1$, $Z_2$ and M, and the $E_2$ moiety, taken with $Z_2$, $Z_3$ and M, each, independently, form heterocycles; $R_{80}$ and $R_{81}$ each independently are absent, or represent one or more covalent substitutions of $E_1$ and $E_2$ with an organic or inorganic substituent permitted by valence requirements of the ring atom to which it is attached, or any two or more of the $R_{80}$ and $R_{81}$ substituents taken together form a bridging substituent; and M represents a transition metal, wherein each $R_1$, $R_2$, $R'_1$, $R'_2$ $R_{80}$ and $R_{81}$ substituents are selected to provide at least one stereogenic center in said tridentate ligand. In preferred embodiments, each $R_{80}$ and $R_{81}$ occurring in 140 independently represent hydrogen, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is zero or an integer in the range of 1 to 8. The metal will generally be coordinated with a counterion (as in the aged catalyst described below).

In certain embodiments, the catalyst complex comprises a tridentate ligand and is represented by general structure 160:

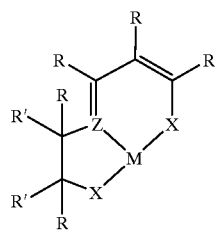

160

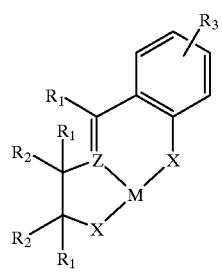

162 wherein

Z represents N, P or As;

X represents independently for each occurrence O, S, Se or ZR;

M represents a metal ion and the requisite number of counterions;

R represents independently for each occurrence hydrogen, alkyl, aryl, halo, acyl or aralkyl; or taken together any two instances of R on adjacent carbons may represent an optionally substituted ring consisting of 3–8 backbone atoms inclusive; said ring being saturated, unsaturated or aromatic; and said ring may be fused to another optionally substituted ring;

R' represents independently for each occurrence hydrogen, alkyl, aryl, halo, acyl or aralkyl; or taken together the two instances of R' may represent an optionally substituted ring consisting of 3–8 backbone atoms inclusive; said ring being saturated, unsaturated or aromatic; and said ring may be fused to another optionally substituted ring; and one or both of the carbons bearing an instance of R' may be asymmetric.

In certain embodiments, the catalyst complex is represented by general structure 160 and the associated definitions, wherein M represents Cr(III).

In certain embodiments, the catalyst complex is represented by general structure 160 and the associated definitions, wherein X represents O.

In certain embodiments, the catalyst complex is represented by general structure 160 and the associated definitions, wherein Z represents N.

In certain embodiments, the catalyst complex is represented by general structure 160 and the associated definitions, wherein X represents O; and Z represents N.

In certain embodiments, the catalyst complex is represented by general structure 160 and the associated definitions, wherein both of the carbons bearing an instance of R' are asymmetric.

In certain embodiments, the catalyst complex is represented by general structure 160 and the associated definitions, wherein X represents O; and both of the carbons bearing an instance of R' are asymmetric.

In certain embodiments, the catalyst complex is represented by general structure 160 and the associated definitions, wherein Z represents N; and both of the carbons bearing an instance of R' are asymmetric.

In certain embodiments, the catalyst complex is represented by general structure 160 and the associated definitions, wherein M represents Cr(III); X represents O; Z represents N; and both of the carbons bearing an instance of R' are asymmetric.

In certain embodiments, the catalyst complex comprises a tridentate ligand and is represented by general structure 162:

wherein

X represents independently for each occurrence O, S, Se or $ZR_1$;

Z represents independently for each occurrence N, P or As;

M represents a metal ion and the requisite number of counterions;

$R_1$ represents independently for each occurrence hydrogen, alkyl or aryl;

$R_2$ represents independently for each occurrence hydrogen, alkyl or aryl; and taken together the two instances of $R_2$ may represent an optionally substituted ring consisting of 3–8 backbone atoms inclusive; said ring being saturated, unsaturated or aromatic; and said ring may be fused to another optionally substituted ring;

$R_3$ may be absent or present between one and four times inclusive;

$R_3$ represents independently for each occurrence alkyl, aryl, aralkyl, halo, acyl, sulfonyl, $-(C(R_1)_2)_m COR_1$, $-(C(R_1)_2)_m CO_2R_1$, $-(C(R_1)_2)_m NO_2$, $-(C(R_1)_2)_m S(O)_n R_1$, $-(C(R_1)_2)_m OR_1$, $-(C(R_1)_2)_m N(R_1)_2$;

n represents independently for each occurrence an integer in the range 0–3 inclusive;

m represents independently for each occurrence an integer in the range 0–8 inclusive; and one or both of the carbons bearing an instance of $R_2$ may be asymmetric.

In certain embodiments, the catalyst complex is represented by general structure 160 and the associated definitions, wherein M represents Cr(III).

In certain embodiments, the catalyst complex is represented by general structure 162 and the associated definitions, wherein Z represents N.

In certain embodiments, the catalyst complex is represented by general structure 162 and the associated definitions, wherein X represents O.

In certain embodiments, the catalyst complex is represented by general structure 162 and the associated definitions, wherein X represents O; and Z represents N.

In certain embodiments, the catalyst complex is represented by general structure 162 and the associated definitions, wherein both carbons bearing $R_2$ are asymmetric.

In certain embodiments, the catalyst complex is represented by general structure 162 and the associated definitions, wherein X represents O; Z represents N; and both carbons bearing $R_2$ are asymmetric.

In certain embodiments, the catalyst complex is represented by general structure 162 and the associated definitions, wherein $R_1$ represents hydrogen.

In certain embodiments, the catalyst complex is represented by general structure 162 and the associated definitions, wherein X represents O; Z represents N; both carbons bearing $R_2$ are asymmetric; and $R_1$ represents hydrogen.

In certain embodiments, the catalyst complex is represented by general structure 162 and the associated definitions, wherein M represents Cr(III); X represents O; Z represents N; both carbons bearing $R_2$ are asymmetric; $R_1$ represents hydrogen; and $R_3$ is present once or twice and represents alkyl.

For example, a chiral tridentate catalyst useful in the subject stereoselective reactions can have a ligand represented by the general formula:

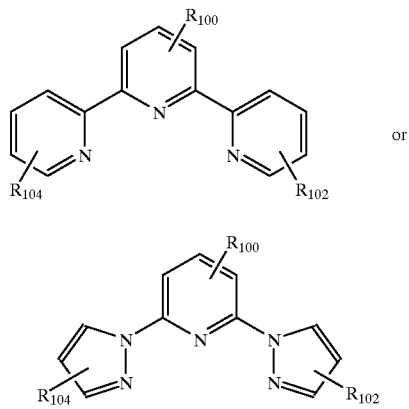

142 or

144 wherein each of $R_{100}$, $R_{102}$ and $R_{104}$ each independently are absent, or represent one or more covalent substitutions of heterocycle to which it is attached, or any two or more of the substituents taken together form a bridging substituent; wherein each $R_{100}$, $R_{102}$ and $R_{104}$ substituents, if present, can be selected from the group consisting of halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is zero or an integer in the range of 1 to 8. Again, the substitution of 142 is intended to provide at least one stereogenic center in the tridentate ligand. Exemplary embodiments of the 2,2':6', 2"-terpyridine ligands 142 and their synthesis can be adapted from, for example, Potts et al. (1987) *J. Am Chem Soc* 109:3961; Hadda et al. (1988) *Polyhedron* 7:575; Potts et al. (1985) *Org Synth* 66:189; and Constable et al. (1988) *Inorg Chim Acta* 141:201. Exemplary 2,6-bis(N-pyrazolyl) pyridine ligands 144 can be adapted from, for example, Steel et al. (1983) *Inorg Chem* 22:1488; and Jameson et al. (1990) *J. Org Chem* 55:4992.

Yet another class of planar tridentate catalyst useful in the subject stereoselective reactions can have a ligand represented by the general formula:

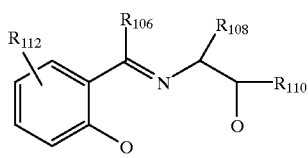

146 wherein each of $R_{106}$, $R_{108}$ and $R_{110}$ can be selected from the group consisting of hydrogens, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{112}$ is absent or represent one or more covalent substitutions of the heterocycle to which it is attached; or any two or more of the $R_{106}$, $R_{108}$, $R_{110}$ and $R_{112}$ substituents taken together form a bridging substituent; $R_7$ represents an aryl, a cycloalkyl, a cycloalkenyl, a heterocycle or a polycycle; and m is zero or an integer in the range of 1 to 8. The choice of substitution of 146 is intended to enhance its chirality. Exemplary embodiments of the salicylaldehyde-derived ligands 146 and their synthesis can be adapted from, for example, Desimoni et al. (1992) *Gazzetta Chimica Italiana* 122:269.

In a preferred embodiment, the tridentate ligand is given by the general formula 150

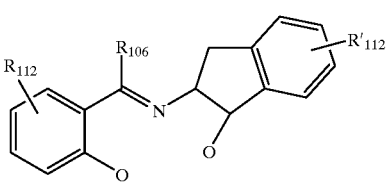

150 wherein $R_{106}$ represents a hydrogen, halogen, alkyl, alkenyl, alkynyl, hydroxyl, alkoxyl, silyloxy, amino, nitro, thiol amine, imine, amide, phosphonate, phosphine, carbonyl, carboxyl, silyl, ether, thioether, sulfonyl, selenoether, ketone, aldehyde, ester, or —$(CH_2)_m$—$R_7$; and each of $R_{112}$ and $R'_{112}$ is absent or represent one or more covalent substitutions of the heterocycle to which it is attached, such as designated for $R_{106}$; $R_7$ represents an aryl, a cycloalkyl, a cycloalkenyl, a heterocycle or a polycycle; and m is zero or an integer in the range of 1 to 8. For example, as described in the appended examples, a preferred salicylaldehyde-derived ligand is given by the general formula 152

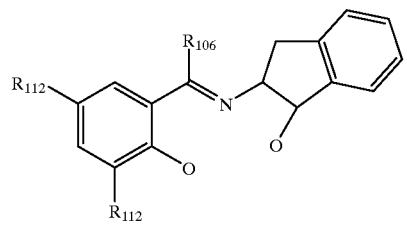

152 each $R_{112}$ being independently selected.

Still another class of planar tridentate catalyst useful in the subject stereoselective reactions can have a ligand represented by the general formula:

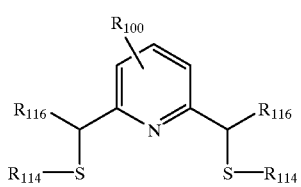

148 wherein $R_{100}$ is as described above, and each $R_{116}$ and $R_{114}$ can be selected from the group consisting of hydrogens, halogens, alkyls, alkenyls, alkynyls, hydroxyl, alkoxyl, silyloxy, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; or any two or more of the substituents taken together form a bridging substituent; $R_7$ represents an aryl, a cycloalkyl, a cycloalkenyl, a heterocycle or a polycycle; and m is zero or an integer in the range of 1 to 8. The choice of substitution of 148 is intended to provide at least one stereogenic center in the tridentate ligand. Exemplary embodiments of the salicylaldehyde-derived ligands 148 and their synthesis can be adapted from, for example, Marangoni et al. (1993) *Polyhedron* 12:1669.

C. Tuning the Catalysts

The ligand substituents are chosen to optimize the selectivity of reaction and the catalyst stability. The exact mechanism of action of the metallosalenate-catalyzed cycladdition reactions has not yet been precisely elucidated. However, the need for stereoselective nonbonded interactions between the substrate and catalyst is a feature of this and other chiral planar catalysts of the subject reaction. While not wishing to be bound by any particular theory, it is believed that the present cycloaddition reactions involve two factors largely responsible for induction of asymmetry by formation of stereospecific nonbonded pairs of catalyst and substrate, namely, steric and electronic interactions between a substrate and the ligand of the chiral catalyst. In general, "tuning" refers altering the steric bulk of the ligand to limit the approach of the substrate, utilizing steric repulsions between the substrate and ligand substituents, and altering the electronic characteristics of the ligand to influence electronic interactions between the substrate and the ligand, as well as the rate and mechanism of the catalyzed reaction. For instance, the choice of appropriate substituents as "blocking groups" enforces certain approach geometries and disfavors others.

Furthermore, the choice of substituent may also affect catalyst stability; in general, bulkier substituents are found to provide higher catalyst turnover numbers. It has been found that for the asymmetric epoxidation of olefins by Mn(salen) complexes, t-butyl groups (or other tertiary groups) are suitable bulky moieties for optimizing stereoselectivity and increasing catalyst turnover.

A preferred embodiment for each of the embodiments described above provides a catalyst having a molecular weight less than 10,000 g/m (a.m.u.), more preferably less than 5000 g/m, and even more preferably less than 2500 g/m. In another preferred embodiment, none of the substituents of the core ligand, or any molecule coordinated to the metal in addition to the ligand, have molecular weights in excess 1000 g/m, more preferably they are less than 500 g/m, and even more preferably, are less than 250 g/m. The choice of substituent on the ligand can also be used to influence the solubility of the catalyst in a particular solvent system.

As mentioned briefly above, the choice of ligand substituents can also affect the electronic properties of the catalyst. Substitution of the ligand with electron-rich (electron-donating) moieties (including, for example, alkoxy or amino groups) increases the electron density of the ligand and at the metal center. Conversely, electron-withdrawing moieties (for example, chloro or trifluoromethyl) on the ligand result in lower electron density of the ligand and metal center. The electron density of the ligand is important due to the possibility of interactions (such as r-stacking) with the substrate (see, e.g., Hamada et al. *Tetrahedron* (1994) 50:11827). The electron density at the metal center may influence the Lewis acidity of the metal. Choice of appropriate substituents thus makes possible the "tuning" of the reaction rate and the stereoselectivity of the reaction.

IV. Substrates

Substrates which are useful in the present invention may be determined by the skilled artisan according to several criteria. In general, suitable substrates will have one or more of the following properties: 1) They will be capable of participating in a cycloaddition reaction under the subject conditions; 2) Said cycloaddition reaction will yield a useful product; 3) They will not react at undesired functionalities; 4) They will react at least partly through a mechanism catalyzed by the chiral catalyst; 5) They will not undergo significant further undesired reaction after reacting in the desired sense; 6) They will not substantially react with or degrade the catalyst, e.g. at a rate greater than conversion of the substrate. It will be understood that while undesirable side reactions (such as catalyst degradation) may occur, the rates of such reactions can be manipulated through the selection of reactants and conditions; these manipulations will render the undesired side reactions slow in comparison with the rate of the desired reaction(s).

In certain embodiments, the reactive substrates may be contained in the same molecule, thereby resulting in an intramolecular cycloaddition reaction.

As discussed above, a wide variety of substrates are useful in the methods of the present invention. The choice of substrates will depend on factors such as the desired product, and the appropriate substrates will be apparent to the skilled artisan. It will be understood that the substrates preferably will not contain any interfering functionalities. In general, appropriate substrates will contain either a reactive π-bond or a reactive 1,3-diene moiety.

V. Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the substrate, the catalyst, or the product. For example, the reaction temperature influences the speed of the reaction, as well as the stability of the reactants and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent (see Example 8, infra). Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed. In certain embodiments, ethereal solvents are preferred.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. The partial pressure of the reactive gas may be from 0.1 to 1000 atmospheres, more preferably from 0.5 to 100 atm, and most preferably from about 1 to about 10 atm. In certain embodiments it is preferable to perform the reactions under an atmosphere of an inert gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, derivativation with one or more of substituents of the ligand. The immobilized ligands can be complexed with the desired metal to form the chiral metallocatalyst. The catalyst, particularly the "aged" catalyst described herein (Example 8, infra), is easily recovered after the reaction as, for instance, by filtration or centrifugation.

EXEMPLIFICATION

The invention now being generally described, it will be more readily understood by reference to the following examples which are included merely for purposes of illustration of certain aspects and embodiments of the present invention, and are not intended to limit the invention.

Example 1

Highly Diastereo- and Enantioselective Formal hetero-Diels-Alder Reactions Catalyzed by Tetradentate Chromium Catalysts The formal hetero-Diels-Alder reaction between 1-methoxy-3-[(trimethylsilyl)oxy]-1,3-butadiene (1, "Danishefsky's diene") and aldehydes provides useful access to dihydropyranones (2, eq. 1), a class of compounds with extensive utility in organic synthesis.[1] Recently, several groups have reported enantioselective catalytic versions of this reaction.[2] In most cases, these condensations have been shown not to involve a formal cycloaddition reaction, but rather to proceed via a Mukaiyama aldol condensation followed by cyclization under the influence of acid catalysis to generate 2.[2a,b] Recently we have found that chiral chromium- and cobalt-containing salen complexes catalyze the highly enantioselective reaction of nucleophiles with epoxides.[3] In an effort to ascertain whether other classes of nucleophile-electrophile reactions are promoted by such catalysts, we evaluated a series of chiral (salen)metal complexes for the hetero-Diels-Alder reaction shown in eq. 1, and identified that (salen)Cr(III)Cl complex 3 does indeed catalyze the reaction. Optimization of the catalyst and reaction conditions has led to the development of a protocol for this synthetically important transformation that requires only 2 mol % of readily available chiral catalyst and affords 2 with good enantioselectivity.

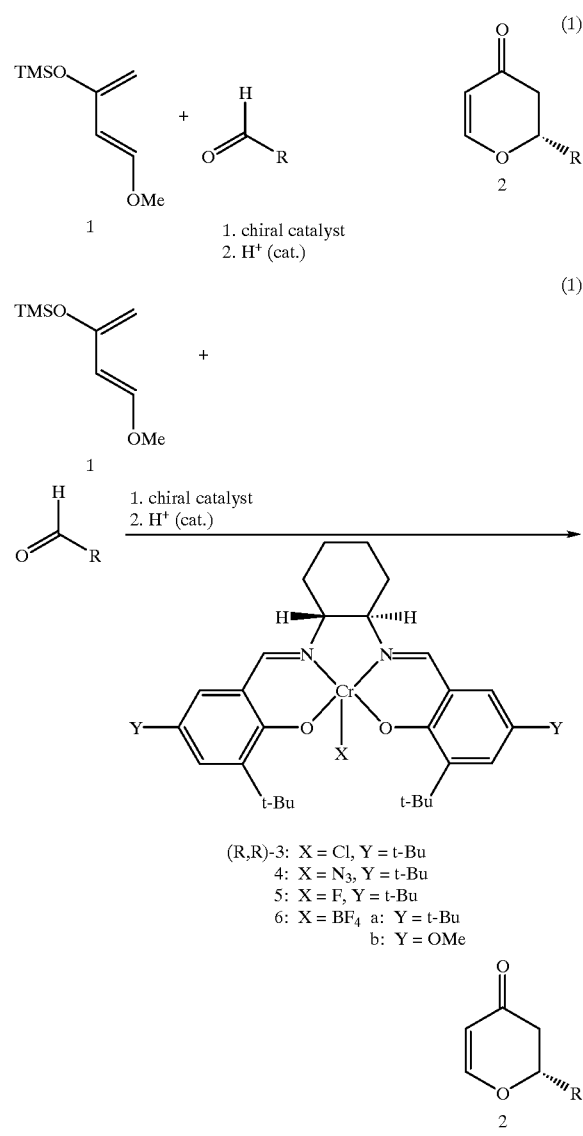

Results and Discussion

Several parameters were found to influence the rate and enantioselectivity of the condensation reaction. Reactions performed in non-coordinating ethereal solvents such as Et$_2$O and TBME afforded the dihydropyranone in the highest yield and enantioselectivity. The reaction of 1 with benzaldehyde in the presence of 2 mol % (R,R)-3 at room temperature yielded R-2a in 96% isolated yield and 56% ee.[4] With an initial substrate concentration of 1.0 M, the reaction required 8 h to attain >90% conversion. At five-fold higher concentration the reaction was complete in 4 h with a slight increase in enantioselectivity (60% ee). A further increase to 64% ee was obtained with 68% isolated yield in reactions carried out at −30° C., although substantially longer reaction times were also required (70% conversion of 1 after 24 h with [1]$_0$=5 M.

The identity of the catalyst counterion was also revealed to be a critical parameter for the attainment of high enantioselectivity. For example, azide complex 4 displayed significantly higher enantioselectivity (81% ee) and yield (86%) at −30° C. relative to chloride catalyst 3 in the model reaction with benzaldehyde. Catalyst 5, bearing the more electronegative fluoride counterion, afforded even higher enantioselectivity (86% ee) although lower product yield (56%). Catalysts bearing less coordinating counterions [X =BF$_4$, PF$_6$, B(Ar$_f$)$_4$ (Ar$_f$=3,5—C$_6$H$_3$(CF$_3$)$_2$] proved to be much less reactive and less enantioselective. However, the addition of oven-dried powdered 4 Å molecular sieves to reactions with these catalysts led to increased yield and enantioselectivities in each case with the best result obtained with the tetrafluoroborate catalyst 6a, which afforded 2a in 87% ee and 85% isolated yield at −30° C. (Table 1, entry a). A brief screen of substitution of the salicylidene component of the salen ligand showed that catalyst 6a, derived from the commercially available t-butyl-substituted salen ligand, was the most effective although the methoxy-substituted catalyst 6b conferred measurably higher enantioselectivity and yield in select cases (entries e and f).

The scope of the asymmetric condensation of 1 with aldehydes proved to be quite broad (Table 1). Although enantioselectivity in excess of 90% was achieved only in one case (entry b), several of the dihydropyranone products could be recrystallized to enantiomeric purity (entries d–g). The simplicity of the experimental procedure and the ready accessibility of the catalysts thus renders this an experimentally attractive method for the preparation of enantioenriched dihydropyranone derivatives.

An important question arises regarding the mechanism of the (salen)Cr-catalyzed condensation of 1 with aldehydes. A Mukaiyama aldol condensation mechanism has been identified in the highly effective asymmetric versions of this reaction developed by Keck and by Corey, whereas a concerted [4+2] cycloaddition pathway was indicated in the Eu(hfc)$_3$-catalyzed reaction reported by Danishefsky.[5] In the present (salen)Cr catalytic system, the $^1$H NMR spectrum of the crude reaction product of 1 with benzaldehyde catalyzed by complex 3 revealed the exclusive presence of cycloadduct 7 (eq. 2). To test the possible intermediacy of a Mukaiyama aldol condensation adduct, silyl ether 8 was synthesized independently[6] and subjected to the conditions of the Cr(salen)-catalyzed condensation reaction. However, no detectable cyclization of 8 to 7 was observed after exposure to 2 mol % of catalyst 3 for 6 h at room temperature. These results point toward a concerted [4+2] mechanism for the (salen)Cr catalysts, and thus extend the scope of enantioselective reactions catalyzed by these complexes to the important arena of cycloaddition chemistry.

TABLE 1

Asymmetric Hetero-Diels-Alder Reactions of Diene 1 Catalyzed by 6a and 6b.[a]

| entry | R | temp (° C.) | cat. 6a ee (%)[b] | cat. 6a yield (%)[c] | cat. 6b ee (%)[b] | cat. 6b yield (%)[c] |
|---|---|---|---|---|---|---|
| a | Ph | −30 | 87 | 85 | 65 | 98 |
| b | C$_6$H$_{11}$ | −20 | 93 | 71 | 85 | 76 |
| c | n—C$_5$H$_{11}$ | −40 | 83 | 86 | 62 | 85 |
| d | 2-furyl | −10 | 76 (99) | 89 (63) | 68 | 80 |
| e | E—PhCH=CH | 0 | 70 | 65 | 73 (99) | 96 (64) |
| f | p—BrC$_6$H$_4$CH$_2$OCH$_2$ | −30 | 79 | 67 | 84 (99)[d] | 94 (70)[d] |
| g | o—ClC$_6$H$_4$CO$_2$CH$_2$ | −20 | 83 (99)[d] | 92 (67)[d] | 72 | 86 |

[a]Unless noted otherwise, all reactions were run at 5.0 M in TBME using 2 mol % catalyst, 1.0 mmol of aldehyde, 1.0 mmol of diene 1, and 300 mg of oven dried 4 Å molecular sieves for 24 h.
[b]Enantiomeric excesses in parentheses were obtained after recrystallization (see Experimental).
[c]Yields in parentheses refer to crystallized yields.
[d]Reactions were run on 10.0 mmol scale.

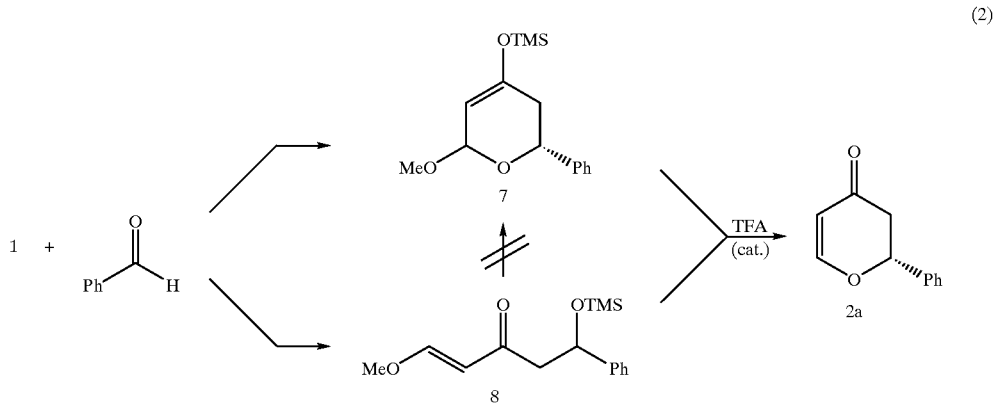

(2)

Experimental Procedures for Example 1
Preparation of (R,R)-6a

To a solution of (R,R)-3 (632 mg, 1.00 mmol) in TBME (10 mL) was added AgBF$_4$ (195 mg, 1.00 mmol). The reaction flask was wrapped with aluminum foil and stirred at rt for 5 h after which it was filtered through Celite and washed with TBME. Evaporation of the solvent gave 680 mg (0.99 mmol, 99%) of a brown solid, which was used without further purification. IR (KBr, cm$^{-1}$) 2952, 1621, 1534, 1436, 1392, 1361, 1319, 1255, 1171, 1062; Exact mass (FAB) calcd for C$_{36}$H$_{52}$N$_2$O$_4$Cr [M—BF$_4$]$^+$: 596.3434; found: 596.3450.

Preparation of (R,R)-6b

Under a nitrogen atmosphere, CrCl$_2$ (86 mg, 0.70 mmol) was added to (R,R)-2,2'-[(1,2-cyclohexanediyl)bis(nitrilomethylidyne)]bis[4-methoxy-6-(1,1-dimethylethyl)phenol][7] (ligand of 6b, 285 mg, 0.580 mmol) in dry, degassed THF (10 mL). The resulting mixture was stirred under nitrogen for 3 h, at which time the flask was opened to air and allowed to stir for an additional 16 h at room temperature. The solution was diluted with TBME and rinsed with sat'd NH$_4$Cl (5×50 mL) and sat'd NaCl (1×50 mL). The organic phase was separated, dried over Na$_2$SO$_4$, filtered, and concentrated in vacuo. The resulting residue was dissolved in TBME (7 mL) and treated with solid AgBF$_4$ (105 mg, 0.537 mmol). The reaction flask was wrapped with aluminum foil and stirred at rt for 5 h. The resulting mixture was filtered through Celite. Solvent removal by rotary evaporation afforded 328 mg (0.520 mmol, 90%) of 6b as a brown solid which was used without further purification. IR (KBr, cm$^{-1}$) 2949, 1623, 1546, 1459, 1422, 1345, 1313, 1175, 1062, 821; Exact mass (FAB) calcd for C$_{30}$H$_{40}$N$_2$O$_4$Cr [M—BF$_4$]$^+$: 544.2393; found: 544.2394.

Preparation of (R,R)-5

To a solution of (R,R)-6a (684 mg, 1.00 mmol) in acetonitrile (10 mL) was added NaF (84 mg, 2.00 mmol). The reaction mixture was stirred at room temperature for 24 h, solvent was removed by rotary evaporation, and the residue suspended in TBME and washed three times with water. The organic phase was dried, filtered through Celite, and evaporated to give 568 mg (0.92 mmol, 92%) of 5 as a brown solid which was used without further purification. IR (KBr, cm$^{-1}$) 2954, 1623, 1533, 1463, 1436, 1392, 1361, 1321, 1256, 1170, 1083, 837; Exact mass (FAB) calcd for C$_{36}$H$_{52}$N$_2$O$_4$Cr [M—F]$^+$: 596.3434; found: 596.3423.

Representative Procedure for the Hetero-Diels-Alder Reaction of 1 with Aldehydes. (R)-2-Phenyl-2,3-dihydro-4H-pyran-4-one (2a)

A 10 mL oven dried flask equipped with a stir bar was charged with (R,R)-6a (13 mg, 0.02 mmol) and 0.3 g of oven dried powdered 4 Å molecular sieves. The flask was sealed with a rubber septum and purged with N$_2$. The catalyst was dissolved in TBME (200 μL) and benzaldehyde (100 μL, 1.0 mmol) was added via syringe at rt. The reaction was then cooled to −30° C. followed by the addition of 1-methoxy-3-[(trimethylsilyloxy)]-butadiene (1) (195 μL, 1.0 mmol). The mixture was allowed to stir at −30° C. for 24 h at which time it was removed from the bath, diluted with 2 mL of CH$_2$Cl$_2$ and treated with a drop of TFA. After stirring 10 min at rt, the reaction was concentrated in vacuo and the crude residue was purified by flash chromatography (7:3 hexanes:EtOAc) to yield 2a[8] (151 mg, 0.85 mmol, 85% yield) as a clear oil. The isolated material was determined to be in 87% ee by chiral GC analysis (Cyclodex-B, 155° C., 20 min, isothermal, t$_R$(minor)=15.4 min, t$_R$(major)=15.7 min). [α]$_D^{26}$−96° (c 0.58, CH$_2$Cl$_2$); lit [2b] −83° for 82% ee material (c 0.5, CHCl$_3$).

(R)-2-Cyclohexyl-2,3-dihydro-4H-pyran-4-one (2b)

The crude product mixture was purified by flash chromatography (7:3 hexanes:EtOAc) to afford 2b in 71% yield (128 mg, 0.71 mmol) as a clear oil. The chromatographed material was determined to be in 93% ee by chiral GC analysis (Cyclodex-B, 150° C., isothermal, t$_R$(minor) =18.7 min, t$_R$(major)=19.3 min). [α]$_D^{26}$−157° (c 1.03, CH$_2$Cl$_2$); lit[2b]−159° for 76% ee material (c 0.5, CHCl$_3$); IR (thin film, cm$^{-1}$) 3498, 2927, 2856, 1677, 1595, 1450, 1408, 1276, 1225, 1038, 992, 910, 794; $^1$H NMR (CDCl$_3$, 400 MHz) δ 7.36 (d, 2H, J=6.0 Hz), 5.38 (dd, 1H, J=1.0 and 6.0 Hz), 4.16 (ddd, 1H, J=3.3, 5.6 and 14.5 Hz), 2.54 (dd, 1H, J=14.5 and 16.7 Hz), 2.38 (ddd, 1H, J=1.0, 3.3 and 16.7 Hz), 1.64–1.81 (m, 6H), 1.00–1.27 (m, 5H); $^{13}$C NMR (CDCl$_3$, 100 MHz) δ 193.3, 163.6, 106.9, 83.6, 41.4, 39.2, 28.2, 26.3, 25.9, 25.8; Exact mass (EI) calcd for C$_{11}$H$_{16}$O$_2$ [M]$^+$: 180.1150; found: 180.1150. The absolute stereochemistry was assigned as (−)-R based on comparison of the measured rotation with the literature value.[2b]

(R)-2-Pentyl-2,3-dihydro-4H-pyran-4-one (2c)

Product 2c was obtained in 86% yield (145 mg, 0.86 mmol) as a clear oil after purification by flash chromatography (8:2 hexanes:EtOAc) and in 83% ee by chiral GC analysis (Cyclodex-B, 120° C., 21 min, 1° C./min to 130° C., t$_R$(minor)=24.5 min, t$_R$(major)=25.2 min). [α]$_D^{26}$−106° (c 0.500, CH$_2$Cl$_2$); IR (thin film, cm$^{-1}$) 2933, 1680, 1596, 1407, 1272, 1230, 1039, 897, 791; $^1$H NMR (CDCl$_3$, 400 MHz) δ 7.36 (d, 2H, J=6.0 Hz), 5.40 (dd, 1H, J=1.1 and 6.0 Hz), 4.36–4.43 (m, 1H), 2.52 (dd, 1H, J=13.4 and 16.7 Hz), 2.42 (dt, 1H, J=2.8 and 12.8 Hz), 1.79–1.83 (m, 1H), 1.64–1.68 (m, 1H), 1.29–1.48 (m, 6H), 0.89 (t, 3H, J=7.0 Hz); $^{13}$C NMR (CDCl$_3$, 100 MHz) δ 192.8, 163.3, 106.9, 79.6, 41.8, 34.3, 31.4, 24.4, 22.5, 13.9; Exact mass (EI) calcd for $C_{10}H_{16}O_2$ [M]$^+$: 168.1150; found: 168.1144. The absolute stereochemistry was assigned as (−)-R by analogy to compounds 2a,b,d.

(R)-2-(2-Furyl)-2,3-dihydro-4H-pyran-4-one (2d)

The crude product mixture was purified by flash chromatography (7:3 hexanes:EtOAc) to yield 2d[5a] in 89% yield (146 mg, 0.89 mmol) as a clear oil which solidified upon standing. The chromatographed material was determined to be 76% ee by chiral GC analysis (Cyclodex-B, 130° C., isothermal, $t_R$(minor)=20.5 min, $t_R$(major)=21.1 min). A single recrystallization from 1:2 $Et_2O$:hexanes yielded 103 mg (63%) of white needle-like crystals in 99% ee by GC analysis. $[\alpha]_D^{26}$ −357° (c 0.805, $CH_2Cl_2$); lit[2b] −255° for 67% ee material (c 0.5, CHCl$_3$).

(R)-2-E-Styryl-2,3-dihydro-4H-pyran-4-one (2e)

The crude residue obtained from the reaction was purified by flash chromatography (7:3 hexanes:EtOAc) to afford 2e[8] in 96% yield (191 mg, 0.96 mmol) as a clear oil which solidified after standing. The isolated material was determined to be 84% ee by chiral HPLC analysis (Chiralcel OD, 9:1 hexanes:IPA, 1.5 mL/min, $t_R$(minor)=11.2 min, $t_R$(major)=26.7 min). Recrystallization from a minimal amount of 4:1 $Et_2O$:hexanes at 0° C. yielded 128 mg (64%) of opaque needle like crystals in 99% ee by HPLC analysis. $[\alpha]_D^{26}$ −215° (c 0.36, $CH_2Cl_2$). The absolute stereochemistry was assigned as (−)-R by analogy to compounds 2a,b,d.

(R)-2-{[(4-Bromophenyl)methoxy]methyl}-2,3-dihydro-4H-pyran-4-one (2f)

Using 2.29 g (10.0 mmol) of [(4-bromophenyl)methoxy]acetaldehyde,[9] the crude residue from the reaction was purified by flash chromatography (7:3 hexanes:EtOAc) to yield 2f (2.81 g, 9.39 mmol, 94% yield) as a clear oil, which solidified upon standing, in 84% ee by chiral HPLC analysis (Chiralcel OD, 9:1 hexanes:IPA, 1 mL/min, $t_R$(minor)=11.3 min, $t_R$(major)=12.8 min). Recrystallization from a minimal amount of $Et_2O$ at 0° C. yielded 2.09 g (70%) of opaque cube like crystals in 99% ee by HPLC analysis. $[\alpha]_D^{26}$ −112° (c 1.74, CHCl$_3$); IR (KBr, cm$^{-1}$) 2852, 1674, 1662, 1590, 1487, 1410, 1291, 1227, 1129, 1093, 1041, 890, 786; $^1$H NMR (CDCl$_3$, 400 MHz) δ 7.48 (d, 2H, J=8.3 Hz), 7.37 (d, 1H, J=6.0Hz), 7.21 (d, 2H, J=8.3 Hz), 5.42 (d, 1H, J=6.0 Hz), 4.56–4.62 (m, 3H), 3.66–3.74 (m, 2H), 2.74 (dd, 1H, J=14.2 and 16.8 Hz), 2.40 (dd, 1H, J=3.4 and 16.8 Hz); $^{13}$C NMR (CDCl$_3$, 100 MHz) δ 192.3, 162.8, 136.5, 131,6, 129.3, 121.8, 107.2, 107.1, 78.2, 72.8, 70.8, 38.3; Exact mass (CI) calcd for $C_{13}H_{17}BrNO_3$ [M+NH$_4$]$^+$: 314.0392; found: 314.0390. The absolute stereochemistry was assigned as (−)-R by analogy to compounds 2a,b,d.

(R)-2-{[(2-Chlorobenzoyl)oxy]methyl}-2,3-dihydro-4H-pyran-4-one (2 g)

Using 1.99 g (10.0 mmol) of [(2-chlorobenzoyl)oxy]acetaldehyde,[10] the crude residue from the reaction was purified by flash chromatography (7:3 hexanes:EtOAc) to yield 2 g (2.44 g, 9.20 mmol, 92% yield) as a clear oil which solidified upon standing. The chromatographed material was determined to be 83% ee by chiral HPLC analysis (Chiralcel OD, 9:1 hexanes:IPA, 1 mL/min, $t_R$(minor)=20.6 min, $t_R$(major)=23.4 min). Recrystallization from a minimal amount of $Et_2O$ at 0° C. yielded 1.78 g (67%) of opaque white crystals that were 99% ee by HPLC analysis. $[\alpha]_D^{26}$ −144° (c 0.508, CHCl$_3$); IR (KBr, cm$^{-1}$) 3068, 2958, 1740, 1681, 1592, 1407, 1298, 1270, 1215, 1141, 1123, 1055, 1041, 1028, 977, 872, 799; $^1$H NMR (CDCl$_3$, 400 MHz) δ 7.84 (d, 2H, J=6.0 Hz), 7.2–7.5 (m, 4H), 5.45 (dd, 1H, J=0.9 and 6.0 Hz), 4.76 (m, 1H), 4.60 (dd, 1H, J=3.4 and 12.2 Hz), 4.53 (dd, 1H, J=5.6 and 12.2 Hz) 2.78 (dd, 1H, J=14.0 and 17.6 Hz), 2.53 (ddd, 1H, J=0.9,3.6 and 17.6 Hz); $^{13}$C NMR (CDCl$_3$, 100 MHz) δ 190.9, 165.0, 162.5, 133.8, 133.0, 131.6, 131.2, 129.1, 126.6, 107.3, 76.0, 65.2, 38.2; Exact mass (CI) calcd for $C_{13}H_{11}ClO_4$ [M]$^+$: 266.0346; found: 266.0346. The absolute stereochemistry was assigned as (−)-R by analogy to compounds 2a,b,d.

REFERENCES FOR EXAMPLE (1) For reviews see: (a) Danishefsky, S. J. *Chemtracts* 1989, 273. (b) Danishefsky, S. J.; De Ninno, M. P. *Angew. Chem., Int. Ed. Engl.* 1987, 26, 15. (c) Danishefsky, S. J. *Aldrich. Acta.* 1986,19, 59.

(2) (a) Keck, G. E.; Li, X. Y.; Krishnamurthy, D. *J. Org. Chem.* 1995, 60, 5998. (b) Corey, E. J.; Cywin, C. L.; Roper, T. D. *Tetrahedron Lett.* 1992, 33, 6907. (c) Ghosh, A. K.; Mathivanan, P.; Cappiello, J. *Tet. Lett.* 1997, 38, 2427. (d) Matsukawa, S.; Mikami, K. *Tetrahedron Asymm.* 1997, 8, 815. (e) Gao, Q.; Maruyama, T.; Mouri, M.; Yamamoto, H. *J. Org. Chem.* 1992, 57, 195 1. (f) Togn i, A. *Organometallics* 1990, 9, 3106.

(3) (a) Martinez, L. E.; Leighton, J. L.; Carsten, D. H.; Jacobsen, E. N. *J. Am. Chem. Soc.* 1995, 117, 5897. (b) Larrow, J. F.; Schaus, S. E.; Jacobsen, E. N. *J. Am. Chem. Soc.* 1996, 118, 7420. (c) Jacobsen, E. N.; Kakiuchi, F.; Konsler, R. G.; Larrow, J. F.; Tokunaga, M. *Tetrahedron Lett.* 1997, 38, 773. (d) Tokunaga, M.; Larrow, J. F.; Kakiuchi, F.; Jacobsen, E. N. *Science* 1997, 277, 936.

(4) The absolute stereochemistry was assigned by comparison of the optical rotation with literature values (ref. 2a,b).

(5) (a) Bednarski, M.; Danishefsky, S. J. *J. Am. Chem. Soc.* 1983, 105, 3716. (b) Bednarski, M.; Danishefsky, S. J. *J. Am. Chem. Soc.* 1983, 105, 6968. (c) Bednarski, M.; Maring, C; Danishefsky, S. J. *Tetrahedron Lett.* 1983, 23, 3451.

(6) Compound 8 was prepared independently by the reaction of 1 with benzaldehyde in the presence of BF$_{3O}$OEt$_2$. Danishefsky, S. J.; Larson, E.; Askin, D.; Kato, N. *J. Am. Chem. Soc.* 1985, 107, 1246.

(7) Pospisil, P. J.; Carsten, D. H.; Jacobsen, E. N. *Chem. Eur. J.* 1996, 2, 974.

(8) Sher, F.; Isidor, J. L.; Taneja, H. R.; Carlson, R. M. *Tetrahedron Lett.* 1973, 8, 577.

(9) Prepared by a procedure analogous to the one described for [(4-methoxyphenyl)methoxy]acetaldehyde in: England, P.; Chun, K. H.; Moran, E. J.; Armstrong, R. W.; *Tetrahedron Lett.* 1990, 31, 2669.

(10) Prepared by a procedure analogous to the one described for (4-chlorobenzoyl)oxy]acetaldehyde in: Hashiguchi, S.; Maeda, Y.; Kishimoto, S.; Ochiai, M. *Heterocycles* 1986, 24, 2273.

Example 2

Highly Diastereo- and Enantioselective Formal hetero-Diels-Alder Reactions Catalyzed by Novel Tridentate Chromium Catalysts As part of a program directed towards the total synthesis of natural products and relying on metal-catalyzed asymmetric reactions, we chose to study the formal hetero-Diels-Alder reaction (HDA) of (2Z,4E)-3-trialkylsilyloxy substituted 2,4-hexadienes (7a–d) with aldehydes.[1] Studies reported in the literature to date have focused primarily on the reaction of highly reactive diene 1-methoxy-3-(trimethylsilyloxy)-butadiene (Danishefsky's diene) with aldehydes[2] and, more recently, with ketones.[3] In this manner, dihydropyranones (DHPs) bearing one new stereocenter are constructed. While these compounds are valuable educts for asymmetric synthesis, we saw the value in studying less reactive dienes, e.g., those bearing one oxygen substituent, that would yield in the HDA tetrahydropyranones (THPs) with upwards of four stereocenters. The stereocenters are set in a controlled manner in a single operation that provides stereochemically complex synthetic intermediates from simple achiral starting materials.

A previous study within this group established that the chromium(III) salen complex 1a was a convenient and enantioselective catalyst for the reaction of Danishefsky's diene with a range of aldehydes.[4,5]

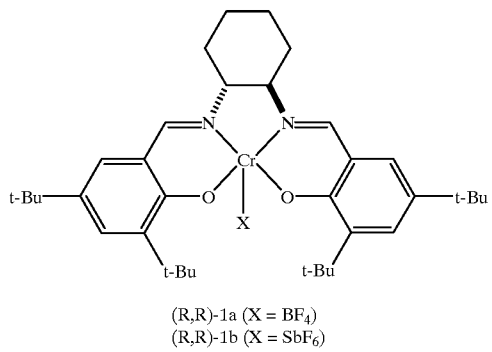

(R,R)-1a (X = BF$_4$)
(R,R)-1b (X = SbF$_6$)

Using these conditions as a starting point, we discovered that (2Z,4E)-3-trialkylsilyloxy-2,4-hexadienes (7a–d) underwent cycloaddition with benzaldehyde to give the corresponding THPs 8 (R$^2$=Ph) in good enantioselectivity and excellent diastereoselectivity (70–82% e.e. and >95% d.e.).[6] Maximum selectivity was obtained when 7a was reacted with benzaldehyde at room temperature as a neat mixture in the presence of catalyst 1b[7] to give 8 (R$^2$=Ph) in 82% e.e., >95% d.e. and 50% isolated yield.[8] However, when aliphatic aldehydes, such as (t-butyldimethylsilyloxy)acetaldehyde (TBSOCH$_2$CHO), were used only poor enantioselectivities (24% e.e.) were obtained under catalysis by either 1a or 1b.

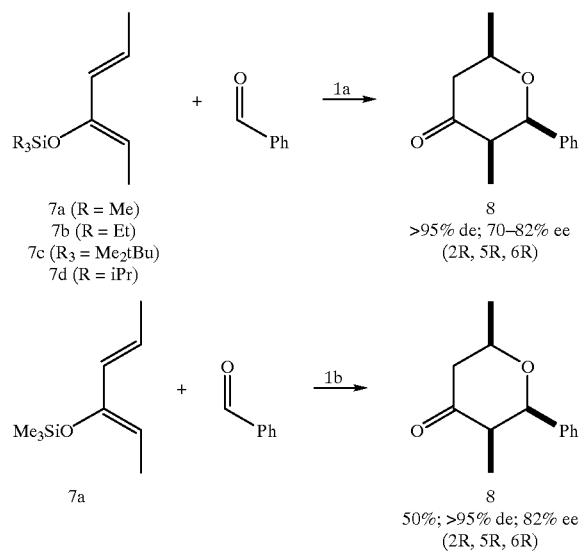

At this juncture we elected to study tridentate chromium (III) complexes such as 2. Early experiments using catalyst 2 with benzaldehyde and TBSOCH$_2$CHO gave superior results, affording 8 (R$^2$=Ph) and 9 (R$^2$=CH$_2$OTBS) in 80% e.e. and 57% e.e., respectively. An enantioselectivity screen showed that an increase in the size of the group ortho to the phenolic oxygen gave increased asymmetric induction. This observation led ultimately to the synthesis of a ligand bearing a 1-adamantyl group at this position.[10] These novel catalysts (6a–c) proved remarkably enantio- and diastereoselective for both aromatic and aliphatic aldehydes.

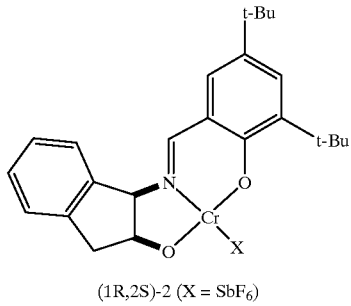

(1R,2S)-2 (X = SbF$_6$)

Both enantiomers of catalyst 6a were prepared from commercially available 2-adamantyl-4-methylphenol 3 by the route outlined in Scheme 1. Counterion metathesis was accomplished using standard literature methods to yield the Cr(III)F-containing catalyst (6b) and the Cr(III)SbF$_6$-containing catalyst (6c), the latter having a shelf life of 2 weeks when stored in a dessicator. We are developing a protocol for preparing this catalyst in situ.[12,13]

Scheme 1

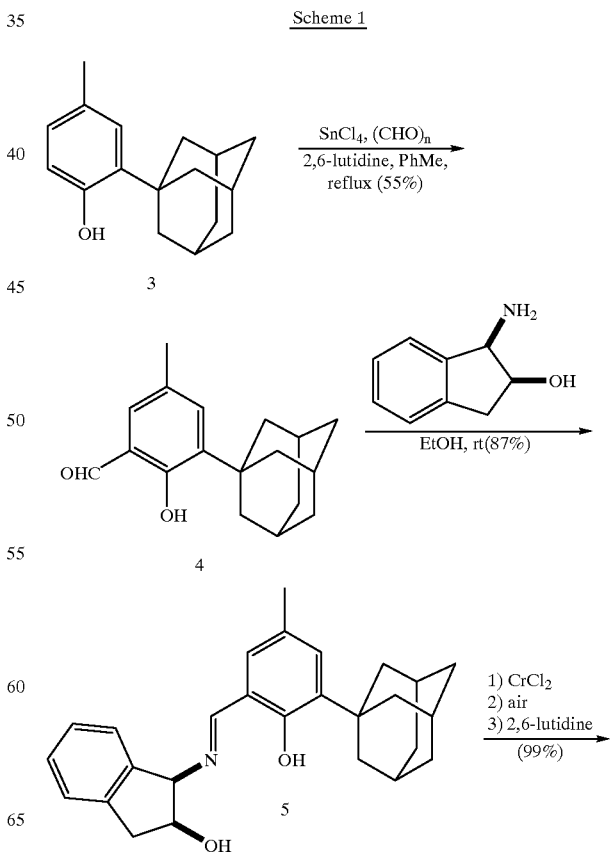

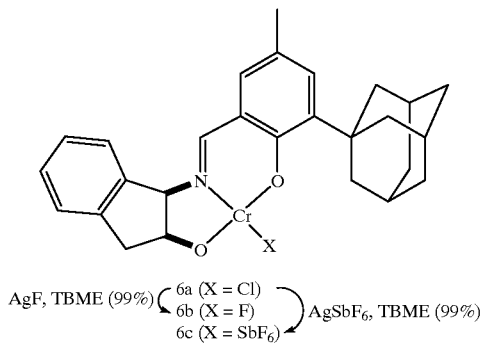

AgF, TBME (99%) ⟨ 6a (X = Cl)
6b (X = F) ⟩ AgSbF$_6$, TBME (99%)
6c (X = SbF$_6$)

Our preliminary experiments using catalyst 6a with diene 7b and TBSOCH$_2$CHO produced outstanding results, yielding DHP 8 (R$^2$=CH$_2$OTBS) in 88% isolated yield, >95% d.e. and 98% e.e. after 24 hours reaction time at room temperature using only 0.5 mol % of the catalyst (Table 1, Entry a). However, we were disappointed to find the reaction of 7b with benzaldehyde gave THP 8 (R$^2$=Ph) in only 65% e.e. The more reactive catalyst 6c gave an improved enantioselectivity of 81% e.e., but both reductions in temperature and increases in catalyst loading failed to improve upon this result. Up to this point all reactions had been conducted in the absence of solvent. After a screen of solvents it was found that acetone[14] gave a dramtic enhancement in enantioselectivity in the reaction with benzaldehyde, affording the THP 8 (R$_2$=Ph, entry g) in 90% e.e.[15]

TABLE 1

Catalytic Enantioselective Hetro-Diels-Alder reaction between alkylsilyloxy substituted 2,4-hexadienes and representative aldehydes.

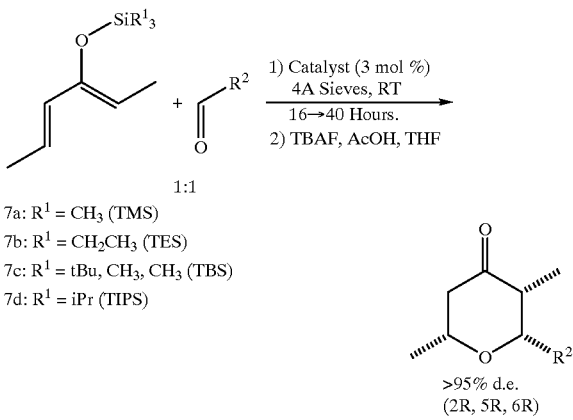

7a: R$^1$ = CH$_3$ (TMS)
7b: R$^1$ = CH$_2$CH$_3$ (TES)
7c: R$^1$ = tBu, CH$_3$, CH$_3$ (TBS)
7d: R$^1$ = iPr (TIPS)

>95% d.e.
(2R, 5R, 6R)

| entry | diene | product 8$^a$ R$^2$ = | acetone | cat (mol %) | yield (%)$^b$ | e.e. (%)$^c$ |
|---|---|---|---|---|---|---|
| a | 7b | CH$_2$OTBS | x | 6a (0.5) | 88 | 98 |
|   |    |             | ✓ | 6a (3.0) | 90 | 99 |
|   |    |             | x | 6c (3.0) | 93 | 97 |
|   |    |             | ✓ | 6c (3.0) | 97 | >99 |
| b | 7b | CH$_2$OBn | ✓ | 6c (3.0) | 89 | 94 |
| c | 7b | C$_5$H$_{11}$ | x | 6c (3.0) | 85 | 97 |
| d | 7b | (CH$_2$)$_4$CH=CH$_2$ | x | 6c (3.0) | 78 | 97 |
| e | 7b | CH$_2$CH$_2$Ph$^e$ | ✓ | 6c (3.0) | 78 (84)$^d$ | 98 |
| f | 7b | CH$_2$CH$_2$NHBOC | ✓ | 6c (3.0) | 28 (31)$^d$ | 96 |
| g | 7b | Ph | ✓ | 6c (3.0) | 72 (80)$^d$ | 90 |
| h | 7b | 2-furyl | ✓ | 6c (3.0) | 77 (86)$^d$ | 95 |
| i | 7a | C$_5$H$_{11}$ | x | 6c (3.0) | 81 | 98 |
| j | 7c | C$_5$H$_{11}$ | x | 6c (3.0) | 93 | 96 |
| k | 7d | C$_5$H$_{11}$ | x | 6c (3.0) | 77 | 94 |

$^a$Relative stereochemistry was determines by nOe NMR experiments. For determination of absolute stereochemistry see Supplementary Material.
$^b$Isolated yields after flash column chromatography on silica el
$^c$Enantiomeric excess determined by GLC (Cylcodex-β column).
$^d$Number in ( ) conversion after 40 hours.
$^e$2 equiv. of aldehyde used With these reaction conditions in hand, a range of aldehydes were screened (Table 1).[16] Aliphatic and aromatic aldehydes all performed with exceptional enantioselectivities (entries a–h) using either catalyst 6a or 6c. In most cases, employing acetone as solvent gave optimal enantioselectivities, however, a catalyst loading of 3.0 mol % was required to ensure a high conversion after 40 hours reaction time in some cases. It is of special note that all the reactions were performed at ambient temperature and required 4A molecular sieves for optimal results.[17] In all cases the diastereoselectivity was greater than 95% in favor of the endo cyclization product. The catalysts appear to be somewhat tolerant of functionality as evidenced by the BOC protected amino-aldehyde (entry f) despite poor conversion to the THP 8 (R$^2$=CH$_2$CH$_2$NHBOC). The structure of the trialkylsilyl group of the diene (7) appears to have only a slight effect on the e.e. and yield of the cycloaddition product (entries c, i and j). Only a slight reduction in selectivity and rate was observed using a TIPS group (diene 7d, entry k). Unfortunately, sterically hindered aliphatic aldehydes such as iso-butylaldehyde and cyclohexane carboxaldehyde did not undergo cyclization with diene 7b. Conjugated aldehydes such as cinnamaldehyde were also ineffective, producing complex mixtures of products.

We further explored the scope of this cycloaddition reaction by examining other reactive dienes (Table 2). TBSOCH$_2$CHO was selected as the aldehyde component of this study due to its high reactivity, selectivity and synthetic utility. (3E)-2-Triethylsilyloxy-1,3-pentadiene (9) when treated with TBSOCH$_2$CHO in the presence of catalyst 6a gave outstanding selectivity, yielding the corresponding THP 10 in 78% yield in 98% e.e. and 98% d.e. (Table 2, entry a). We tested Danishefsky's diene 12 using our catalytic system for comparison with literature examples.[4] The DHP 12 was obtained in 84% e.e. using acetone as solvent (entry b, Table 2). However, when the same reaction was attempted using hexanal, THP 13 was isolated in an optimal 97% e.e. using the fluoride catalyst 6b (entry c, Table 2). This represents a great improvement over our earlier 1-trimethysilyloxybutadiene 16 afforded only low conversion or complex mixtures of product depending on the catalyst used. However, a small amount (<10%) of the lactone 17 was isolated in excellent e.e. after oxidation (entry e, Table 2).[18]

TABLE 2

Enantioselective Hetero-Diels-Alder Reactions: Variation of the Diene.

| entry[a] | diene | product | acetone | catalyst | yield (%)[b] | ee (%)[c] |
|---|---|---|---|---|---|---|
| a | 9 (OTES diene) | 10 | yes | 6a | 78 | 98 (2R, 6R) |
| b | 11 (MeO, OTES diene) | 12 | yes | 6a | 89 | 84 (R) |
| c | 11 (MeO, OTES diene) | 13 (C₅H₁₇) | no | 6b | 77 | 97 (R) |
| d | 14 (MeO diene) | 15 | no | 6a | 91 | >99 (R) |
| e | 16 (TMSO diene) | 17 | no | 6a | <10 | 96 (R) |

[a]All reactions were performed on 1.0 mmol scale using 4A sieves at rt with reaction times between 16 and 40 h.
[b]The products were purified by flash chromatography on silica gel after quenching the reactions by addition of TFA in $CH_2Cl_2$ or TBAF/AcOH in THF.
[c]Enantiomeric excesses was determined by chiral chromatography and the absolute configurations were inferred by comparison with the literature.

results.[4] Reaction of our model aldehyde with 1-methoxybutadiene in the presence of catalyst 6a (3 mol %) cleanly afforded the methoxy acetal adduct 15 in 91% yield with exceptional selectivity (97% d.e. and >99% e.e.) in under 16 hours reaction time at RT. We were pleased to find that the catalyst loading could be reduced to 0.5 mol % with no loss in selectivity and an extended reaction time of 40 hours.[18] Unfortunately, the less expensive We briefly probed the mechanism of the catalyzed reaction by looking for a non-linear dependance of product e.e. on catalyst e.e.[19] In the case of reaction between diene 7b and $TBSOCH_2CHO$ catalyzed by 6a, a linear relationship between the level of asymmetric induction and the entiomeric excess of the catalyst was observed. The same linear effect was found when acetone was used as solvent. Based on these two relationships, we infer that either a monomeric chromium(III) species, or a multimeric species which does not deaggregate during the course of the reaction, catalyzes the reaction.

In conclusion, we have developed a highly effective system for the asymmetric HDA that uses novel chromium catalysts at low loading (0.5–3.0 mol %). The catalysts gave excellent reactivity, levels of asymmetric induction, and high diastereoselectivity with less electron-rich dienes than those previously studied, yielding synthetically useful THP products. Although the mechanism and mode of action of this novel system are as yet unknown, efforts are underway to illuminate them, as well as to expand the scope of this catalytic system.

References and Footnotes for Example 2.

(1) For reviews, see : (a) Danishefsky, S. J. Chemtracts 1989, 273. (b) Danishefsky, S. J.; De Ninno, M. P. Angew. Chem., Int. Ed. Engl. 1987,26, 15. (c) Danishefsky, S. J.; Aldrichimica Acta. 1986, 19, 59. (d) Boger, D. L. In Comprehensive Organic Synthesis; Trost, B. M. Fleming, I., Eds.; Pergamon Press: Oxford, 1991; Vol. 5 pp 451–512. (e) Boger, D. L. ; Weinreb, S. M. Hetero Diels-Alder Methodology in Organic Synthesis; Academic Press: San Diego, Calif., 1987.

(2) (a) Matsukawa, S.; Mikami, K. Tetrahedron Asymm. 1997, 8, 815. (b) Ghosh, A. K.; Mathivanan, P.; Cappiello, J. Tetrahedron Lett. 1997, 38, 2427. (c) Keck, G. E.; Li, X. Y.; Krishnamurthy, D. J. Org. Chem. 1995, 60, 5998. (d) Corey, E. J.; Cywin, C. L.; Roper, T. D.; Tetrahedron Lett. 1992, 33, 6907. (e) Gao, Q.; Maruyama, T.; Mouri, M.; Yamamoto, H. J. Org. Chem. 1992, 57, 1951. (f) Maruoka, K.; Itoh, T.; Shirasaka, T.; Yamamoto, H.; J. Am. Chem. Soc. 1988, 110, 310. (g) Motoyama, Y.; Terada, M.; Mikami, K. Synlett 1995, 967.

(3) (a) Johannsen, M.; Yao, S.; Jorgensen, K. A. Chem. Commun. 1997, 2169. (b) Johannsen, M.; Yao, S.; Audrain, H.; Hazell, R. G.; Jorgensen, K. A. J. Am. Chem. Soc. 1998, 120, 8599.

(4) Schaus, S. E.; Branalt, J.; Jacobsen, E. N.; J. Org. Chem. 1998, 63, 403.

(5) Cobalt(II) salen complexes have been used recently for asymmetric HDA: Li, L-S.; Wu, Y.; Hu, Y-J.; Xia, L-J.; Wu, Y-L. Tetrahedron Asymm. 1998,9,2271.

(6) The alkylsilyloxy dienes were prepared by literature methods: Synthesis, 1976, 259.

(7) Counterion exchange to $SbF_6$— with other catalyst systems has provided greatly improved selectivity and reactivity, see: (a) Evans, D, A.; Murry, J. A.; von Matt, P.; Norcross, R. D.; Miller, S. J. Angew, Chem., Int. Ed. Engl. 1995, 34, 798. (b) Evans, D, A.; Murry, J. A.; Kozlowski, M. C. J. Am. Chem. Soc. 1996, 118, 5814. (c) Evans, D. A.; Kozlowski, M. C.; Burgey, C. S.; MacMillan, D. W. C. J. Am. Chem. Soc. 1997, 119, 7893.

(8) (2Z, 4E)-3-Triethylsilyloxy-2,4-hexadiene was used in later experiments as it gave the best combination of enantioselectivity and isolated yield.

(10) Zhang, W. PhD Thesis, University of Illinois, September 1991.

(12) In general with older batches of catalyst 6c enantioselectivies would remain the same but reactivity was lost.

(13) Early results to date have shown that pre-stirring the chromium(III) chloride catalyst 6a with $NaSbF_6$ generates a catalytic system that gives identical enantioselectivity as 6c.

(14) (a) Earlier research on an unrelated project using acetone as a solvent with tridente chromium(III) catalysts had given enhanced enantioselectivities. Zhen, L.; Jacobsen, E. N.; unpublished results. (b) Zhen, L. PhD Thesis, University of Harvard, March 1997.

(15) Ethereal solvents such as TBME and diethyl ether did not alter the selectivity or the rate of the reaction however non-polar solvents such as benzene, hexane and halogenated solvents such as $CH_2Cl_2$ reduced the selectivity of the reaction.

(16) Representative procedure for catalysed cycloaddition: 3-Triethylsilyloxy-2,4-hexadiene (72% pure, 342 ul, 1.38 mmol) was added to a stirred mixture of (t-butyldimethylsilyloxy)acetaldehyde (200 ul, 1.00 mmol), the catalyst (15 mg, 0.03 mmol) and 4A sieves (200 mg) under $N_2$ at RT. The mixture was stirred for 16 hours then diluted with THF (4 mL), cooled to 0 C then AcOH (114 ul, 2.00 mmol) was added followed by TBAF (1.5 ml 1.50 mmol). After 30 min the mixture was diluted with 2:1 hexanes/diethyl ether (60 ml) and washed successively with water (2×30 ml), sat. aq. $NaHCO_3$ (30 ml) and brine (30 ml). The solution was dried ($MgSO_4$), concentrated in vacuo and the product isolated by flash chromatography on silica gel (5% ether/hexanes) to give a colorless oil (273 mg, 97%).

(17) The reaction listed in Table 1, entry a when performed in the absence of 4A molecular sieves gave the THP 9 (R=$CH_2OTBS$) in 73% conversion after 40 hours at RT and a slightly lower selectivity of 94% e.e.

(18) The enantioselectivity was determined chiral GLC separation of an a,b-unsaturated lactone derivative prepared by PDC, AcOH oxidation of the methoxyacetal 15 in an overall yield of 55% for the two steps.

(19) Casiraghi, G.; Casnati, G.; Puglia, G.; Sartori, G.; Terenghi, G.; J. Chem. Soc. Perkin Trans 1.1980, 1862.

Example 3

Preparation of (R,R)-1,2-Diphenyl-1,2-bis(3-tert-butylsalicylideamino)ethane

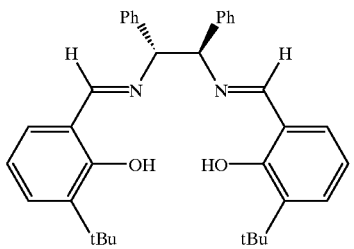

A solution of 360.5 mg (2.0 mmol) of 3-tert-butylsalicylaldehyde in 3 ml of EtOH was added dropwise to a solution of 212.3 mg (1.0 mmol) of (R,R)-1,2-diamino-1,2-diphenylethane in 5 ml of EtOH. The reaction mixture was heated to reflux for 1 h and water (5 ml) was added. The oil that separated solidified upon standing. Recrystallization from MeOH/$H_2O$ gave 485.8 mg (91%) of yellow powder, mp 73–74° C. $^1H$ NMR (CDCl$_3$) δ 1.42 (s, 18H, CH$_3$), 4.72 (s, 2H, CHN=C), 6.67–7.27 (m, 16H, ArH), 8.35 (s, 2H, CH=N), 13.79 (s, 2H, ArOH) ppm; $^{13}C$ NMR (CDCl$_3$) δ 29.3, 34.8, 80.1, 117.8, 118.5, 127.5, 128.0, 128.3, 129.6, 130.1, 137.1, 139.5, 160.2, 166.8 ppm. Anal. Calcd. for $C_{36}H_{40}N_2O_2$. C, 81.17; H, 7.57; N, 5.26. Found: C, 81.17; H, 7.60; N, 5.25.

Example 4

Preparation of (R,R)-1,2-Diphenyl-1,2-bis(3-diphenylmethylsilylsalicylideamino)ethane

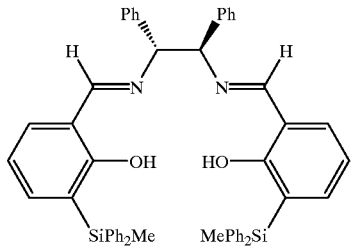

3-(Diphenylmethylsilyl)salicylaldehyde was prepared from 2-bromophenol in 5 steps according to established procedures. A solution of 348.3 mg (1.09 mmol) of 3-(diphenylmethylsilyl)salicylaldehyde and 116.0 mg (0.546 mmol) of (R,R)-1,2-diamino-1,2-diphenylethane in 5 ml of ethanol was heated to reflux for 0.5 h. A bright yellow oil separated from the solution and it solidified upon standing. The mixture was filtered and the yellow solid was washed with 2×5 ml ethanol. The isolated yield of product pure by $^1$H NMR analysis was 416 mg (97%). $^1$H NMR (CDCl$_3$) δ 0.95 (s, 3H), 4.68 (s, 2H), 6.72–7.55 (m, 36H, ArH), 8.37 (s, 2H), 13.34 (s, 2H) ppm.

Example 5

Preparation of 2,2'-Bis(3-tert-Butylsalicylideamino)-1,1'-Binaphthyl

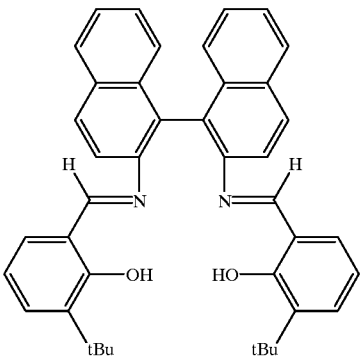

A solution of 725 mg (4.0 mmol) of 3-tert-butylsalicylaldehyde in 6 ml of EtOH was added dropwise to a solution of 569 mg (2.0 mmol) of (+)-2,2'-diamino-1,1'-binaphthyl in 5 ml of EtOH. The reaction mixture was heated to reflux for 8 h and then volatile materials were removed under vacuum. The residue was purified by flash chromatography on 80 g SiO$_2$, using 20% CH$_2$Cl$_2$ in hexane as eluent. The mobile yellow fraction was collected and solvents were removed under vacuum to give 725 mg (1.20 mmol, 59% yield) of the diimine as a yellow powder.

Example 6

Preparation of (S,S)-1,2,-bis(3,5-di-tert-butylsalicylide-amino)cyclohexane (2)

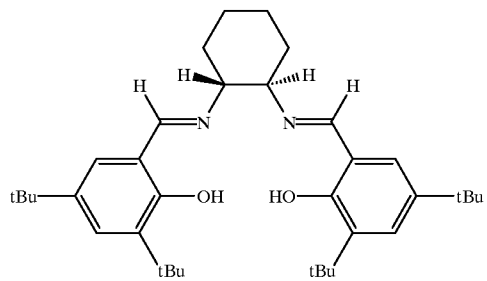

3,5-Di-t-butylsalicylaldehyde (2.0 equivalents) (prepared from the inexpensive, commercially available 2,4-di-t-butylphenol according to Larrow, J. F.; Jacobsen, E. N.; Gao, Y.; Hong, Y.; Nie, X.; Zepp, C. M. J. Org Chem 1994, 59, 1939) was added as a solid to a 0.2 M solution of (S,S)-1,2-diaminocyclohexane (1.0 equivalent) (Aldrich Chemical Co., Milwaukee, Wis.) in absolute ethanol. The mixture was heated to reflux for 1 hr. and then H$_2$O was added dropwise to the cooled bright yellow solution. The resulting yellow crystalline solid was collected by filtration and washed with a small portion of 95% ethanol. The yield of analytically pure salen ligand 2 obtained in this manner was 90–97%.

Spectroscopic and analytical data for the salen ligand: $^1$H NMR (CDCl$_3$) δ 13.72 (s, 1H), 8.30 (S, 1H), 7.30 (d, J=2.3 Hz, 1H), 6.98 (d, J=2.3 Hz, 1H), 3.32 (m, 1H), 2.0–1.8 (m, 2H), 1.8–1.65 (m, 1H), 1.45 (m, 1H), 1.41 (s, 9H), 1.24 (s, 9H). $^{13}$C NMR (CDCl$_3$): δ 165.8, 158.0, 139.8, 136.3, 126.0, 117.8, 72.4, 34.9, 33.0, 31.4, 29.4, 24.3. Anal. Calcd. for C$_{36}$H$_{54}$N$_2$O$_2$: C, 79.07; H, 9.95; N, 5.12. Found: C, 79.12; H, 9.97; N, 5.12.

Example 7

Preparation of (R,R)- and (S,S)-[1,2-bis(3,5-di-tert-butylsalicylideamino)cyclohexane]-manganese(III) chloride The salen ligand synthesized in Example 4 is redissolved in hot absolute ethanol to give a 0.1 M solution. Solid Mn(OAc)$_2$·4H$_2$O(2.5 equivalents) is added in one portion and the solution is refluxed for 1 hr. Approximately 5 equivalents of solid LiCl are then added and the mixture is heated to reflux for an additional 0.5 hr. Cooling the mixture to 0° C. and addition of a volume of water equal to the volume of the brown ethanolic solution affords the Mn(III) complex as a dark brown powder which is washed thoroughly with H$_2$O, and isolated by filtration in 81–93% yield. Acceptable C, H, N, Cl and Mn analyses of the catalyst have been obtained (±0.4%), but these vary according to the extent of water and ethanol incorporation in the powdery product. The solvent content of the catalyst does not influence its effectiveness.

Analytical data for this catalyst: Anal. Calcd for C$_{36}$H$_{52}$ClMnN$_2$O$_2$·C$_2$H$_5$OH: C, 67.19; H, 8.31; Cl, 5.22; Mn, 8.09; N, 4.12: Observed: C, 67.05; H, 8.34; Cl, 5.48; Mn, 8.31; N,4.28.

Example 8

Preparation of (R,R)-[1,2-bis(3,5-di-tert-butylsalicylideamino)cyclohexane]-chromium(III) chloride ((R,R)-1)

The following procedure was found to provide 1 with reproducible catalytic activity. Under a nitrogen atmosphere, 0.309 g (2.52 mmol) of CrCl$_2$ (anhydrous, 99.9%, Alfa/Johnson Matthey) was added to the (R,R)-ligand 2 synthesized in Example 4 (1.25 g, 2.29 mmol) in dry, degassed THF (45 mL). The resulting dark brown solution was stirred under N$_2$ for 3 h and then in air for an additional 3 h. The solution was then diluted with 250 ml of t-butyl methyl ether and washed with satd. NH$_4$Cl (3×150 ml) and brine (3×150 ml). The organic phase was dried (Na$_2$SO$_4$) and solvent was removed under reduced pressure, affording 1.41 g (87% yield) of 1 as a brown solid which was >98% pure as determined by HPLC analysis (octadecyl reverse phase, 100% CH$_3$CN). This material was used in the ring opening reactions without further purification. Recrystallization from acetonitrile provided high quality orange-brown crystals with 63% recovery: mp 375–398° C. (dec). IR (KBr, cm$^{-1}$) 3610 (br), 3420 (br), 2951(s), 2866, 1619(s), 1531, 1434, 1390, 1321, 1255, 1170, 1030, 837, 785, 748, 563, 543. Anal. Calcd for C$_{38}$H$_{59}$N$_2$O$_4$CrCl1.3/2H$_2$O.1/2THF: C, 65.64; H, 8.55; N, 4.03; Cr, 7.48; Cl, 5.10. Found: C, 65.72; H, 8.53; N, 4.04; Cr, 7.45; Cl, 5.15. MS (FD): m/z 631 ([M]+). HRMS (FAB): m/z calcd for [C$_{36}$H$_{52}$N$_2$O$_2$Cr]+([1-Cl]+) 596.3418, found 596.3434. $\mu_{eff}$=3.97 $\mu_B$. Conductance (CH$_3$CN, 0.0045M) 0.57 Ω$^{-1}$ cm$^2$ mol$^{-1}$.

Example 9

Synthesis of Catalyst 200

A tridentate catalyst was synthesized as described below and shown in FIG. 2. To a solution of (S,S)-201 ((S,S)-1-amino-2-hydroxyindane) (0.857 g, 5.75 mmol) in 60 ml EtOH was added 202 (1.829 g, 5.75 mmol) under a nitrogen atmosphere. The resulting solution was refluxed under N$_2$ for 12 hours. The solution was then cooled to room temperature, and solvent was removed under reduced pressure. The concentrate was purified by recrystallization from hexane to give 2.15 g–2.46 g (83%–95 yield) of 203.

In a dry Schlenk flask under a nitrogen atmosphere, (S,S)-203 (0.765 g, 1.7 mmol) was dissolved in dry THF (30 ml). 2,6-lutidine (0.730 g, 6.81 mmol, distilled over CaH$_2$) was added to the flask, followed by 0.638 g (1.70 mmol) chromium (III) chloride: tetrahydrofuran complex (1:3, 97%, Aldrich). The resulting dark brown solution was stirred under N$_2$ for 12 hours. The solution was then diluted with 200 ml of t-butyl methyl ether and washed with saturated NH$_4$Cl (4×150 ml) and brine (3×150 ml). The organic portion was dried over Na$_2$SO$_4$, and the solvent was removed under reduced pressure. Catalyst-200 (0.890 mg, 95% yield) was obtained as a dark brown solid.

In a dry Schlenk flask under a nitrogen atmosphere, 200 (0.653 g, 1.22 mmol) was dissolved in azidotrimethylsilane (3 ml). The reaction mixture was stirred under N$_2$ for 12 hours and was then concentrated under reduced pressure to remove excess azidotrimethylsilane and TMSCI, and the resulting Cr—N$_3$ azide catalyst 204 could be used without further purification.

Example 10

Synthesis of a Chiral Porphyrin Ligand

Pyrrole (1.0 equivalents) and salicylaldehyde (1.2 equivalents) are dissolved in propionic acid (1 liter/20 ml pyrrole) and the solution is refluxed for 30 minutes. The reaction mixture is allowed to cool to room temperature and stand for one day. The mixture is filtered and the product is recrystallized to yield 5,10,15,20-tetrakis(2'-hydroxyphenyl) porphyrin.

The above-named porphyrin is dissolved in dimethylformamide, cooled to 0° C., and treated with sodium hydride (4 equivalents). The mixture is stirred for 30 minutes, and then a solution of D-threitol 1,4-ditosylate (Aldrich Chemical Co.) in DMF is added slowly. When the addition is finished, the reaction mixture is stirred for 30 minutes more, then carefully quenched. The organic phase is washed with brine and the solvent is evaporated. The residue is purified by HPLC to yield the chiral porphyrin.

Example 11

Highly Enantio- and Diastereoselective Hetero-Diels-Alder Reactions Catalyzed by New Chiral Tridentate Chromium Catalysts This example describes highly enantio- and diastereoselective hetero-Diels-Alder reactions between both aliphatic and aromatic aldehydes and conjugated dienes catalyzed by a new family of chiral tridentate chromium(III) complexes. Moderately nucleophilic dienes are found to combine with simple aldehydes in the presence of low catalyst loadings and at ambient temperature to afford di- or tetrahydropyranyl products with up to 3 stereogenic centers. In general, >90% ee and near-perfect diastereoselectivities are observed.

The formal hetero-Diels-Alder reaction (HDA) between electron rich dienes and carbonyl compounds[1] has emerged as an important target for asymmetric catalysis. Enantioselective HDA reactions can provide direct access to valuable di- and tetrahydropyran derivatives in optically active form from simple achiral starting materials, with the possibility of setting three stereocenters in the cyclization and two more by elaboration of the double bond in the resultant heterocycle. Successes reported in this area have involved primarily reactions of highly electron-rich dienes such as 1-methoxy-3-(trimethylsilyloxy)-butadiene (Danishefsky's diene) and/or highly electron-deficient dienophiles such as glyoxylate derivatives.[2,3,4] While some of these have already found applications in target-oriented synthesis,[5] it is clear that the use of inherently less nucleophilic or electrophilic cyclization partners in highly stereoselective HDA reactions would expand the utility of this methodology considerably.

Earlier studies had established that the chromium(III) salen complexes (1) are effective enantioselective catalysts for the reaction of Danishefsky's diene with a variety of aldehydes.[2k] We have subsequently discovered that complex 1 also promotes the cycloaddition of the less nucelophilic (2Z, 4E)-trialkylsilyloxy-2,4-hexadienes 2–5 with benzaldehyde (6a, R$^1$=Ph) to give, after desilylation, the corresponding tetrahydropyranone derivative 7a with very high diastereoselectivity (>95% de), albeit with only moderate enantioselectivity (70–82% ee) (Scheme 1). For example, treatment of 2 with benzaldehyde as a neat mixture in the presence of the hexafluoroantimonate derivative 1b afforded 7a in 82% ee and 50% isolated yield. However, when non-aromatic aldehydes such as t-butyldimethylsilyloxyacetaldehyde (6b, R$^1$=TBSOCH$_2$) or benzyloxyacetaldehyde (6c, R$^1$=BnOCH$_2$) were used, poor enantioselectivities (approximately 25% ee and 40% ee, respectively) were obtained.

Scheme 1

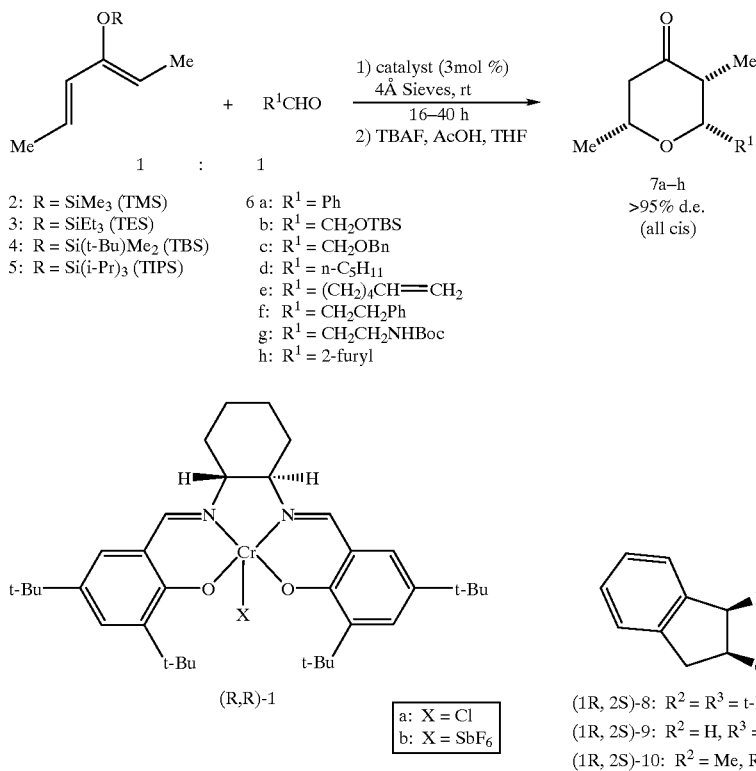

2: R = SiMe₃ (TMS)
3: R = SiEt₃ (TES)
4: R = Si(t-Bu)Me₂ (TBS)
5: R = Si(i-Pr)₃ (TIPS)

6 a: $R^1$ = Ph
  b: $R^1$ = CH₂OTBS
  c: $R^1$ = CH₂OBn
  d: $R^1$ = n-C₅H₁₁
  e: $R^1$ = (CH₂)₄CH=CH₂
  f: $R^1$ = CH₂CH₂Ph
  g: $R^1$ = CH₂CH₂NHBoc
  h: $R^1$ = 2-furyl 7a–h
>95% d.e.
(all cis)

(R,R)-1
a: X = Cl
b: X = SbF₆

(1R, 2S)-8: $R^2 = R^3$ = t-Bu
(1R, 2S)-9: $R^2$ = H, $R^3$ = CEt₂Me
(1R, 2S)-10: $R^2$ = Me, $R^3$ = 1-adamantyl The screen of catalysts was extended to include tridentate Schiff base chromium(III) complexes of the type 8–10 (Table 1).6 The di-tert-butylsalicylaldehyde derived catalyst 8b retained the near-perfect diastereoselectivities exhibited by the tetradentate Cr(III) complexes 5 while affording the tetrahydropyranone products 7a and 7b in superior enantiomeric excess (80% ee and 57% ee, respectively). Catalysts 9a and 9b provided a further increase in enantioselectivity, particularly in the case of aliphatic aldehydes such as 6b (85% ee with 9b).

TABLE 1

Catalytic Enantioselective Hetero-Diels Alder Reactions of Aldehydes and Trialkylsilyloxy Substituted 2,4-Hexadienes.[a]

| entry | diene | aldehyde | conditions[b] | catalyst | yield (%)[c] | e.e. (%)[d] |
|---|---|---|---|---|---|---|
| 1 | 3 | 6a | A | 8b | 50 | 80 |
| 2 | 3 | 6b | A | 8b | n.d. | 57 |
| 3 | 3 | 6b | A | 9b | n.d. | 85 |
| 4 | 3 | 6b | A | 10a[e] | 88 | 98 |
| 5 | 3 | 6b | A | 10b | 93 | 98 |
| 6 | 3 | 6a | A | 10a | n.d. | 65 |
| 7 | 3 | 6a | A | 10b | n.d. | 81 |
| 8 | 3 | 6a | B | 10b | 72 (80)[f] | 90 |
| 9 | 3 | 6b | B | 10a | 90 | 99 |
| 10 | 3 | 6b | B | 10b | 97 | >99 |
| 11 | 3 | 6c | B | 10b | 89 | 94 |
| 12 | 3 | 6d | A | 10b | 85 | 98 |
| 13 | 3 | 6e | A | 10b | 78 | 98 |
| 14 | 3 | 6f[g] | B | 10b | 78 (84)[f] | 98 |
| 15 | 3 | 6g | B | 10b | 28 (31)[f] | 96 |
| 16 | 3 | 6h | B | 10b | 77 (86)[f] | 95 |
| 17 | 2 | 6d | A | 10b | 81 | 98 |
| 18 | 4 | 6d | A | 10b | 93 | 96 |
| 19 | 5 | 6d | A | 10b | 77 | 94 |

[a]Unless noted otherwise, reactions were carried out with 1:1 diene and aldehyde on 1.0 mmol scale with 3 mol % catalyst and powdered 4Å MS for 16–40 hours as outlined in Scheme 1.
[b]A: No solvent added.  B: 200 μL acetone added.
[c]Isolated yields after flash column chromatography on silica gel. In cases where non-optimal catalyst combinations are described, isolated yields were not determined accurately and are therefore not reported (n.d.).
[d]Enantiomeric excesses (ee's) were determined by GC using a commercial (Cylcodex-β) column.
[e]Identical yields and enantioselectivities were obtained when 0.5 mol % catalyst was employed.
[f]Reaction did not reach complete substrate conversion after 40 h. Numbers in parentheses correspond to substrate conversion upon work-up.
[g]Two equiv of aldehyde used.

As part of this examination of the relationship of catalyst structure to reaction enantioselectivity, complex 10a was prepared from readily accessible components as outlined in Scheme 2. Formylation of commercially available phenol 11 by standard protocols,[7] followed by Schiff base formation with cis-1-amino-2-indanol[8] and metal ion complexation afforded the Cr(III)Cl complex in good yield.[9] Counterion metathesis was accomplished with AgSbF₆ in TBME to yield the corresponding hexafluoroantimonate complex 10b.[10]

Scheme 2

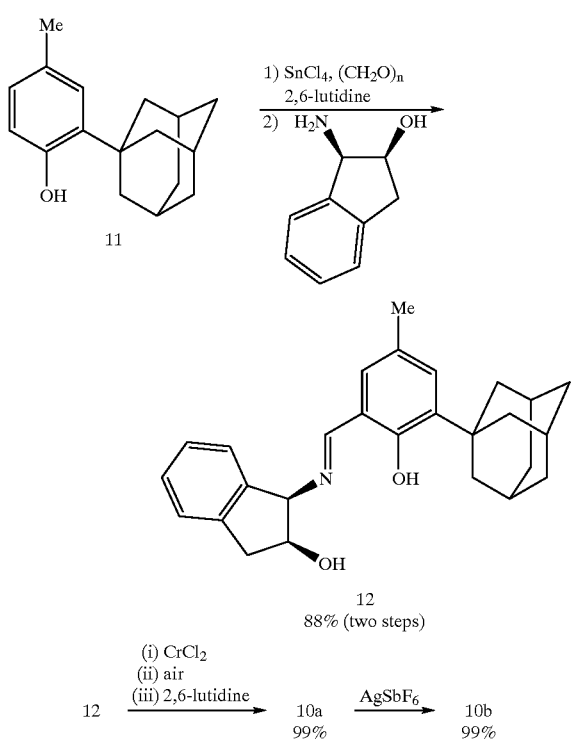

Increasing the size of the salicylaldehyde substituent proximal to the metal center in this fashion provided a remarkable increase in enantioselectivity in HDA reactions between TBSOCH$_2$CHO and diene 3. For example, the reaction of this diene and aldehyde pair yielded tetrahydropyranone 7b in 88% isolated yield, >95% de and 98% ee using only 0.5 mol % of catalyst 10a (Table 1, Entry 4).

However, in contrast to the excellent results obtained with aldehdyde 6b and diene 3, tetrahydropyranone 7a was obtained in only 65% ee in the analogous HDA reaction with benzaldehyde (6a) when chloride complex 10a was employed (entry 6). While the hexafluoroantimonate catalyst 10b proved somewhat more enantioselective (81% ee, entry 7),[11] no further increase was imparted by reducing the reaction temperature or increasing the amount of catalyst used.

Up to this point, all reactions had been evaluated under solvent-free conditions, and a screen of common solvents led to the unexpected discovery that significant enhancement in enantioselectivity in the reaction with benzaldehyde could be attained by the inclusion of acetone (90% ee, entry 8). While the use of this solvent reduces the reaction rate slightly, the enhancement of enantioselectivity appears to be general for aliphatic and aromatic aldehydes.[12]

With these reaction parameters identified, a variety of aldehydes were screened with dienes 2–5 (Table 1). In all reactions, the diastereoselectivity was greater than 95% in favor of the endo cyclization product. Aliphatic and aromatic aldehydes all underwent the HDA cycloaddition with very high enantioselectivities (entries 4–5, 8–19), using either catalyst 10a or 10b. In most cases, reactions using hexafluoroantimonate catalyst 10b were faster and more enantioselective than those in which chloride catalyst 10a was used (data with catalyst 10a not shown). While the use of acetone as solvent was generally beneficial, and critical in the case of aromatic aldehydes, for some substrates use of the solvent-free conditions proved satisfactory (e.g. entries 12–13, 17–19). All of the reactions were performed at ambient temperature and required 4 Å molecular sieves for optimal results.[13] The identity of the trialkylsilyl group of the diene had only a slight effect on the ee and yield of the cycloaddition product (entries 11, 17–19). Unfortunately, sterically hindered aliphatic aldehydes such as isobutyraldehyde and cyclohexanecarboxaldehyde did not undergo cyclization with the diene 3 under the prescribed conditions.

The scope of HDA reactions catalyzed by 10 was evaluated in the context of other substituted diene derivatives (Table 2). Reaction of (2E)-2-triethylsilyloxy-1,3-pentadiene 13 with 6b in the presence of catalyst 10b yielded the corresponding tetrahydropyranone 14 in 78% yield, 98% ee, and 98% de (entry 1). Reaction of 3 with 1-methoxybutadiene (15) in the presence of catalyst 10a (0.5 mol %) also proceeded cleanly and in >99% ee (entry 2).[14] Coupled with hydrolysis and oxidation to the corresponding lactone 17, this method provides highly efficient access to several interesting natural product structures.[15] Catalysis of HDA reactions involving Daneshefsky's diene 18 with catalyst 10 also proceeded with high ee in select cases (entry 4).

TABLE 2

Catalytic Enantioselective Hetero-Diels-Alder Reactions of Selected Dienes and Aldehydes with Catalyst (1R, 2S)-10a.[a]

| entry | diene | product | conditions[a] | yield (%)[b] | ee (%)[c] |
|---|---|---|---|---|---|
| 1 | (structure 13, OTES, Me) | (structure 14, Me, OTBS) | B | 78 | 98 (2R, 6R)[d] |

TABLE 2-continued

Catalytic Enantioselective Hetero-Diels-Alder Reactions of Selected Dienes and Aldehydes with Catalyst (1R, 2S)-10a.[a]

| entry | diene | product | conditions[a] | yield (%)[b] | ee (%)[c] |
|---|---|---|---|---|---|
| 2 | 15 (MeO-diene) | 16 (MeO-, OTBS pyran) | A | 91 | >99 (2S, 6R)[e] |
| 3 | 18 (OTMS, MeO-diene) | 19 (pyranone, OTBS) | B | 89 | 84 (R) |
| 4 | 18 | 20 (pyranone, $C_5H_{17}$) | B | 77 | 90 (R) |

[a]All reactions were carried out as described in footnote a of Table 1.
[b]The products were isolated by treatment with either TFA in $CH_2Cl_2$ at 0° C. or with TBAF, AcOH, THF at 0° C. followed by flash column chromatography on silica gel (see Supporting Information).
[c]Ee's were determined by GLC (Cyclodex-β column). The bases for assignments of relative and absolute configuration are described in the Supporting Information.
[d]98% de.
[e]97% de.

While it might be assumed that a very strong Lewis acid might be required to catalyze such HDA reactions between only moderately nucleophilic dienes and simple aldehydes, no measurable complexation between catalysts 10 and the aldehydes used in this study could be detected by IR spectroscopy. Indeed, the successful use of acetone as a solvent appears inconsistent with a simple Lewis acid mechanism in these reactions.

REFERENCES FOE EXAMPLE 11

(1) For general references on the HDA reaction, see: (a) Danishefsky, S. J. Chemtracts 1989, 273. (b) Danishefsky, S. J. Aldrichimica Acta. 1986, 19, 59. (c) Boger, D. L. In Comprehensive Organic Synthesis; Trost, B. M., Fleming, I., Eds.; Pergamon: New York, 1991; Vol. 5, pp. 451–512. (d) Boger, D. L.; Weinreb, S. M. Hetero Diels-Alder Methodology in Organic Synthesis; Academic Press: San Diego, 1987.

(2) For asymmetric catalytic HDA reactions involving Danishefsky's diene and its analogs, see: (a) Bednarski, M. D.; Maring, C.; Danishefsky, S. J. J. Am. Chem. Soc. 1983, 105, 6968. (b) Maruoka, K.; Itoh, T.; Shirasaka, T.; Yamamoto, H. J. Am. Chem. Soc. 1988, 110, 310. (c) Corey, E. J.; Cywin, C. L.; Roper, T. D. Tetrahedron Lett. 1992, 33, 6907. (d) Gao, Q.; Maruyama, T.; Mouri, M.; Yamamoto, H. J. Org Chem. 1992, 57, 1951. (e) Motoyama, Y.; Mikami, K. J. Chem. Soc., Chem. Commun. 1994, 1563. (f) Keck, G. E.; Li, X. Y.; Krishnamurthy, D. J. Org. Chem. 1995, 60, 5998. (g) Motoyama, Y.; Terada, M.; Mikami, K. Synlett 1995, 967. (h) Ghosh, A. K.; Mathivanan, P.; Cappiello, J. Tetrahedron Lett. 1997, 38, 2427. (i) Matsukawa, S.; Mikami, K. Tetrahedron: Asymmetry 1997, 8, 815. (j) Hanamoto, T. Furuno, H.; Sugimoto, Y.; Inanaga, J. Synlett 1997, 79. (k) Schaus, S. E.; Brånalt, J.; Jacobsen, E. N.; J. Org Chem. 1998, 63, 403. (l) Kobayashi, S.; Komiyama, H.; Ishitani, T. Angew. Chem. Int. Ed. 1998, 37, 979. (m) Li, L-S.; Wu, Y.; Hu, Y-J.; Xia, L-J.; Wu, Y-L. Tetrahedron: Asymmetry 1998, 9, 2271.

(3) For asymmetric catalytic HDA reactions involving glyoxylate, pyruvate, or quinone derivatives as dienophiles, see: (a) Terada, M.; Mikami, K.; Nakai, T. Tetrahedron Lett. 1991, 32, 935. (b) Mikami, K.; Terada, M.; Motoyama, Y.; Nakai, T. Tetrahedron: Asymmetry 1991, 2, 643. (c) Engler, T. A.; Letavic, M. A.; Takusagawa, F. Tetrahedron Lett. 1992, 33, 6731. (d) Mikami, K.; Motoyama, Y.; Terada, M. J. Am. Chem. Soc. 1994, 116, 2812. (e) Johannsen, M.; Jorgensen, K. A. Tetrahedron 1996, 52, 7321. (f) Johannsen, M.; Yao, S.; Jorgensen, K. A. J. Chem. Soc., Chem. Commun. 1997, 2169. (g) Yao, S.; Johannsen, M.; Audrain, H.; Hazell, R. G.; Jorgensen, K. A. J. Am. Chem. Soc. 1998, 120, 8599.

(4) Examples of asymmetric catalytic inverse demand hetero-Diels-Alder reactions have been disclosed recently: (a) Evans, D. A.; Johnson, J. S. J. Am. Chem. Soc. 1998, 120, 4895. (b) Thorhauge, J.; Johannsen, M.;

Jorgensen, K. A. *Angew. Chem. Int. Ed.* 1998, 37, 2404.

(c) Evans, D. A.; Olhava, E. J.; Johnson, J. S.; Janey, J. M. *Angew. Chem. Int. Ed.* 1998, 37, 3372.

(5) For a recent example: Schaus, S. E.; Brånalt, J. E.; Jacobsen, E. N. *J. Org. Chem.* 1998, 63, 4876.

(6) Li, Z. Ph.D. Thesis, Harvard University, 1997.

(7) (a) Casiraghi, G.; Casnati, G.; Puglia, G.; Sartori, G.; Terenghi, G.; *J. Chem. Soc. Perkin Trans* 1. 1980, 1862.
(b) Zhang, W.; Jacobsen, E. N. *J. Org. Chem.* 1991, 56, 2296.

(8) Larrow, J. F.; Roberts, E.; Verhoeven, T. R.; Ryan, K. M.; Senanayake, C. H.; Reider, P. J.; Jacobsen, E. N. *Organic Synth.*, in press. Both enantiomers are available commercially (Aldrich). For a timely review of the use of cis-1-amino-2-indanol in asymmetric synthesis, see: Senanayake, C. H. *Aldrichimica Acta* 1998, 31, 3.

(9) Analysis by low resolution FAB mass spectrometry and IR spectroscopy indicates that 10a exists as a mixture of oligomeric species with water molecules occupying available coordination sites (see Supporting Information).

(10) Preliminary studies have shown that in situ treatment of the chromium(III) chloride catalyst 10a with $NaSbF_6$ generates a catalytic system that gives identical enantioselectivities to those observed with 10b prepared by the route outlined in Scheme 2.

(11) Replacement of coordinating counterions with $SbF_6^-$ has been shown to have significant beneficial effects in other asymmetric catalytic systems. Evans, D, A.; Murry, J. A.; von Matt, P.; Norcross, R. D.; Miller, S. J. *Angew. Chem. Int. Ed.* 1995, 34, 798.

(12) Ethereal solvents such as TBME and diethyl ether did not alter the enantioselectivity or the rate of the reaction, while benzene, hexane and halogenated solvents such as $CH_2Cl_2$ had a detrimental effect.

(13) For example, the reaction listed in entry 5, Table 1, when performed in the absence of 4 Å MS, gave the THP 7b in 73% conversion and 94% ee after 40 hours at rt.

(14) The enantioselectivity was determined chiral GC analysis of lactone 17, prepared by PDC/AcOH oxidation of methoxyacetal 16.

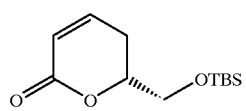

17

(15) For example, (a) callystatin A: Kobayashi, M.; Higuchi, K.; Murakami, N.; Tajima, H.; Aoki, S. *Tetrahedron Lett.* 1997, 38, 2859. Crimmins, M. T.; King, B. W. *J. Am. Chem. Soc.* 1998,120, 9084. (b) Fostriecin A: Boger, D. L.; Hikota, M.; Lewis, B. M. *J. Org. Chem.* 1997, 62, 1748 and references cited therein.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. The catalyst complex represented by general structure 160:

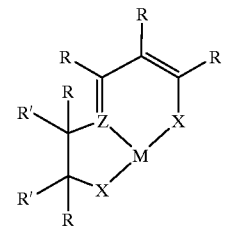

160 wherein

Z represents N, P or As;

X represents independently for each occurrence O, S, Se or ZR;

M represents a metal ion and the requisite number of counterions;

R represents independently for each occurrence hydrogen, alkyl, aryl, halo, acyl or aralkyl; or taken together any two instances of R on adjacent carbons may represent an optionally substituted ring consisting of 3–8 backbone atoms inclusive; said ring being saturated, unsaturated or aromatic; and said ring may be fused to another optionally substituted ring;

R' represents independently for each occurrence hydrogen, alkyl, aryl, halo, acyl or aralkyl; or taken together the two instances of R' may represent an optionally substituted ring consisting of 3–8 backbone atoms inclusive; said ring being saturated, unsaturated or aromatic; and said ring may be fused to another optionally substituted ring; and one or both of the carbons bearing an instance of R' may be asymmetric.

2. The catalyst complex of claim 1, wherein M represents Cr(III).

3. The catalyst complex of claim 1, wherein X represents O.

4. The catalyst complex of claim 1, wherein Z represents N.

5. The catalyst complex of claim 1, wherein X represents O; and Z represents N.

6. The catalyst complex of claim 1, wherein both of the carbons bearing an instance of R' are asymmetric.

7. The catalyst complex of claim 1, wherein X represents O; and both of the carbons bearing an instance of R' are asymmetric.

8. The catalyst complex of claim 1, wherein Z represents N; and both of the carbons bearing an instance of R' are asymmetric.

9. The catalyst complex of claim 1, wherein M represents Cr(III); X represents O; Z represents N; and both of the carbons bearing an instance of R' are asymmetric.

10. The catalyst complex represented by general structure 162:

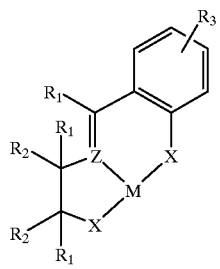

162 wherein

X represents independently for each occurrence O, S, Se or $ZR_1$;

Z represents independently for each occurrence N, P or As;

M represents a metal ion and the requisite number of counterions;

$R_1$ represents independently for each occurrence hydrogen, alkyl or aryl;

$R_2$ represents independently for each occurrence hydrogen, alkyl or aryl; and taken together the two instances of $R_2$ may represent an optionally substituted ring consisting of 3–8 backbone atoms inclusive; said ring being saturated, unsaturated or aromatic; and said ring may be fused to another optionally substituted ring;

$R_3$ may be absent or present between one and four times inclusive;

$R_3$ represents independently for each occurrence alkyl, aryl, aralkyl, halo, acyl, sulfonyl, —$(C(R_1)_2)_m COR_1$, —$(C(R_1)_2)_m CO_2 R_1$, —$(C(R_1)_2)_m NO_2$, —$(C(R_1)_2)_m S(O)_n R_1$, —$(C(R_1)_2)_m OR_1$, —$(C(R_1)_2)_m N(R_1)_2$;

n represents independently for each occurrence an integer in the range 0–3 inclusive;

m represents independently for each occurrence an integer in the range 0–8 inclusive; and one or both of the carbons bearing an instance of $R_2$ may be asymmetric.

11. The catalyst complex of claim 10, wherein M represents Cr(III).

12. The catalyst complex of claim 10, wherein Z represents N.

13. The catalyst complex of claim 10, wherein X represents O.

14. The catalyst complex of claim 10, wherein X represents O; and Z represents N.

15. The catalyst complex of claim 10, wherein both carbons bearing $R_2$ are asymmetric.

16. The catalyst complex of claim 10, wherein X represents O; Z represents N; and both carbons bearing $R_2$ are asymmetric.

17. The catalyst complex of claim 10, wherein $R_1$ represents hydrogen.

18. The catalyst complex of claim 10, wherein X represents O; Z represents N; both carbons bearing $R_2$ are asymmetric; and $R_1$ represents hydrogen.

19. The catalyst complex of claim 10, wherein M represents Cr(III); X represents O; Z represents N; both carbons bearing $R_2$ are asymmetric; $R_1$ represents hydrogen; and $R_3$ is present once or twice and represents alkyl.

20. The catalyst complex represented by 164:

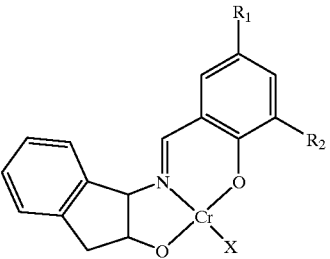

164 wherein $R_1$ and $R_2$ are independently selected from the group consisting of hydrogen, alkyl, aryl, trialkylsilyl, dialkylarylsilyl, alkyldiarylsilyl, triarylsilyl, trialkylstannyl, dialkylarylstannyl, alkyldiarylstannyl and triarylstannyl; and X is the conjugate base of a Bronsted acid with a $pK_a$ less than or equal to 3.

21. The catalyst complex of claim 20, wherein X represents Cl or $SbF_6$.

22. The catalyst complex of claim 20, wherein $R_1$ and $R_2$ are independently selected from the group consisting of hydrogen and alkyl.

23. The catalyst complex of claim 20, wherein X represents Cl or $SbF_6$; and $R_1$ and $R_2$ are independently selected from the group consisting of hydrogen and alkyl.

24. The catalyst complex of claim 20, wherein X represents Cl or $SbF_6$; $R_1$ represents hydrogen, methyl or tert-butyl; and $R_2$ represents tert-butyl, -$CEt_2Me$ or 1-adamantyl.

25. The catalyst complex of claim 20, 21, 22, 23, or 24, wherein the catalyst complex is not a racemic mixture.

26. The catalyst complex of claim 25, wherein the catalyst complex has an enantiomeric excess greater than about 80%.

27. The catalyst complex of claim 25, wherein the catalyst complex has an enantiomeric excess greater than about 90%.

28. The catalyst complex of claim 25, wherein the catalyst complex has an enantiomeric excess greater than about 95%.

* * * * *

UNITED STATES PATENT AND TRADEMARK OFFICE
CERTIFICATE OF CORRECTION

PATENT NO. : 6,369,223 B2 Page 1 of 1
DATED : April 9, 2002
INVENTOR(S) : Jacobsen, E.N. et al.

It is certified that error appears in the above-identified patent and that said Letters Patent is hereby corrected as shown below:

Column 1,
Lines 12-14, replace "The present invention was made with support from the National Institutes of Health; the government, therefor, has certain rights in the invention." with -- This invention was sponsored by NIH Grant No. GM 43214, and the government has certain rights to the invention. --

Signed and Sealed this

Eighth Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,369,223 B2
APPLICATION NO. : 09/755612
DATED : April 9, 2002
INVENTOR(S) : Eric N. Jacobsen et al.

Page 1 of 1

It is certified that error appears in the above-identified patent and that said Letters Patent is hereby corrected as shown below:

In the Specification

At Column 1, Lines 13-15, under the heading Government Funding, please replace:
"The present invention was made with support from the National Institutes of Health; the government, therefore, has certain rights in the invention."

With:
--This invention was made with government support under GM043214 awarded by National Institutes of Health (NIH). The government has certain rights in this invention.--

Signed and Sealed this
Twenty-fifth Day of October, 2022

*Katherine Kelly Vidal*

Katherine Kelly Vidal
*Director of the United States Patent and Trademark Office*